(12) United States Patent
Nishikaze

(10) Patent No.: US 11,105,717 B2
(45) Date of Patent: Aug. 31, 2021

(54) METHOD FOR PREPARING ANALYTICAL SAMPLE, ANALYSIS METHOD, AND KIT FOR PREPARING ANALYTICAL SAMPLE

(71) Applicant: SHIMADZU CORPORATION, Kyoto (JP)

(72) Inventor: Takashi Nishikaze, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 157 days.

(21) Appl. No.: 16/549,020

(22) Filed: Aug. 23, 2019

(65) Prior Publication Data

US 2020/0064235 A1    Feb. 27, 2020

(30) Foreign Application Priority Data

Aug. 24, 2018   (JP) ............................. JP2018-157702

(51) Int. Cl.
*G01N 1/28* (2006.01)
*H01J 49/04* (2006.01)
*G01N 30/04* (2006.01)

(52) U.S. Cl.
CPC .............. *G01N 1/28* (2013.01); *G01N 30/04* (2013.01); *H01J 49/04* (2013.01); *G01N 2560/00* (2013.01)

(58) Field of Classification Search
None
See application file for complete search history.

(56) References Cited

U.S. PATENT DOCUMENTS

2018/0059094 A1    3/2018 Nishikaze

FOREIGN PATENT DOCUMENTS

| EP | 3354158 A2 | 8/2018 |
| EP | 3534158 A1 | 9/2019 |
| JP | 6135710 B2 | 5/2017 |

OTHER PUBLICATIONS

Laura Riboni et al., "Natural Occurrence of Ganglioside Lactones," The Journal of Biological Chemistry, Jun. 25, 1986, pp. 8514-8519, vol. 261, No. 18.
Sheng Liu et al., "Comprehensive N-Glycan Profiling of Cetuximab Biosimilar Candidate by NP-HPLC and MALDI-MS," PLOS ONE, Jan. 10, 2017, pp. 1-14, vol. 12, No. 1.
Takashi Nishikaze et al., "Differentiation of Sialyl Linkage Isomers by One-Pot Sialic Acid Derivatization for Mass Spectrometry-Based Glycan Profiling," Analytical Chemistry, Feb. 21, 2017, pp. 2353-2360, vol. 89, No. 4.
Steven B. Levery et al., "Strategies for Characterization of Ganglioside Inner Esters I-Fast Atom Bombardment Mass Spectrometry," Biomedical and Environmental Mass Spectrometry, 1990, pp. 303-310, vol. 19, No. 5.

(Continued)

*Primary Examiner* — Xiaoyun R Xu
(74) *Attorney, Agent, or Firm* — Sughrue Mion, PLLC

(57) ABSTRACT

A method for preparing an analytical sample for analysis of a glycan that includes a lactone structure and is contained in a sample, includes: performing a first amidation reaction that amidates a sialic acid including the lactone structure through addition of a first amidation reaction solution to the sample, the first amidation reaction solution containing ammonia, an amine, or a salt thereof as a first nucleophilic agent that is reacted with the sialic acid including the lactone structure; and performing a second reaction that modifies at least a part of sialic acids not amidated in the first amidation reaction through a method different from permethylation.

16 Claims, 16 Drawing Sheets

(56) References Cited

OTHER PUBLICATIONS

Takashi Nishikaze et al., "A universal approach to linkage-specific derivatization for sialic acids on glycopeptides," Journal of the American Society for Mass Spectrometry, Jun. 2017, 1 page, vol. 28, No. 1, Supplement Poster No. MP091.

Andrew K. Powell et al., "Stabilization of Sialic Acids in N-linked Oligosaccharides and Gangliosides for Analysis by Positive Ion Matrix-assisted Laser Desorption/Ionization Mass Spectrometry," Rapid Communications in Mass Spectrometry, 1996, pp. 1027-1032, vol. 10, No. 9.

Yoshiaki Miura et al., "Rapid and Simple Solid-Phase Esterification of Sialic Acid Residues for Quantitative Glycomics by Mass Spectrometry," Chem. Eur. J., 2007, pp. 4797-4804, vol. 13, No. 17.

Communication dated Jan. 16, 2020 from the European Patent Office in application No. 19193126.0.

Hanamatsu, H., et al., "Sialic Acid Linkage Specific Derivatization of Glycosphingolipid Glycans by Ring-Opening Aminolysis of Lactones", Analytical Chemistry, 2018, vol. 90, No. 22, pp. 13193-13199.

Nishikaze, T., "Sialic acid derivatization for glycan analysis by mass spectrometry", Proceedings of the Japan Academy, Series B, vol. 95, No. 9, 2019, pp. 523-537.

FIG. 3A    LacA2 (lactone x2)
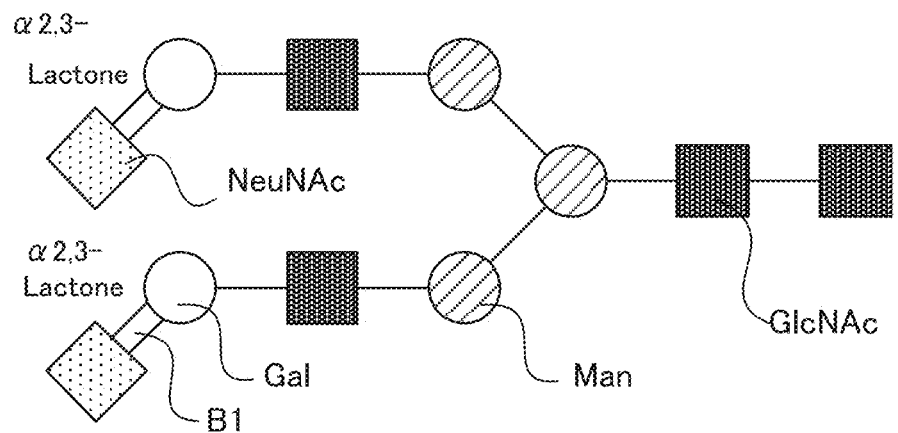
FIG. 3B    33A2 (α2,3- x2)
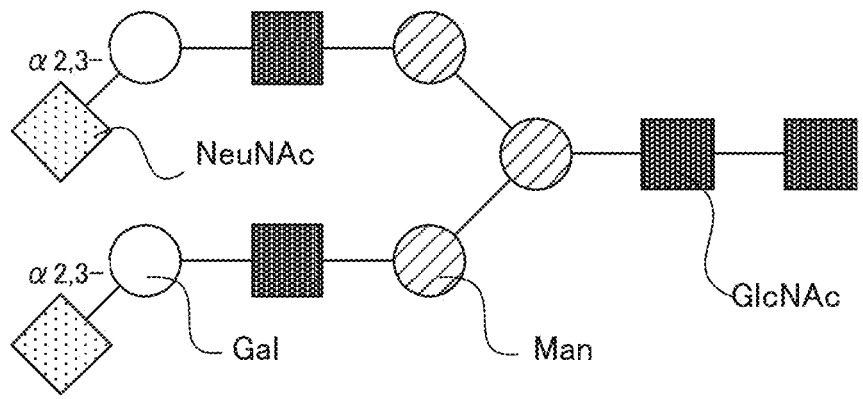
FIG. 3C    66A2 (α2,6- x2)
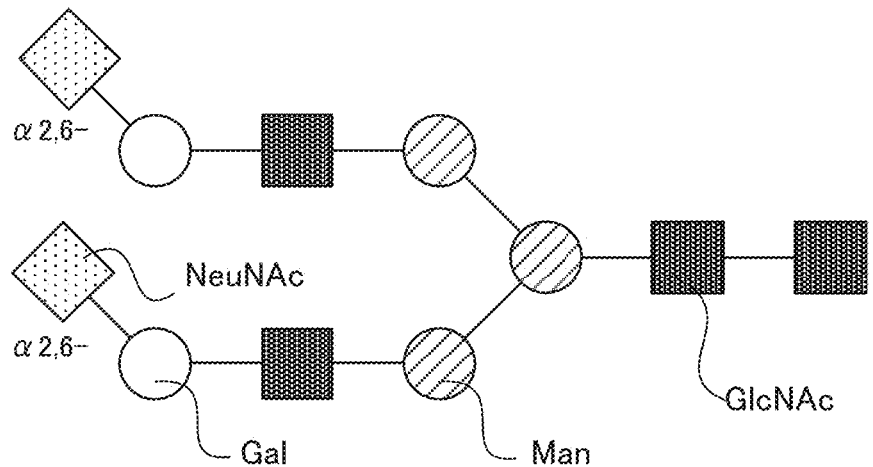

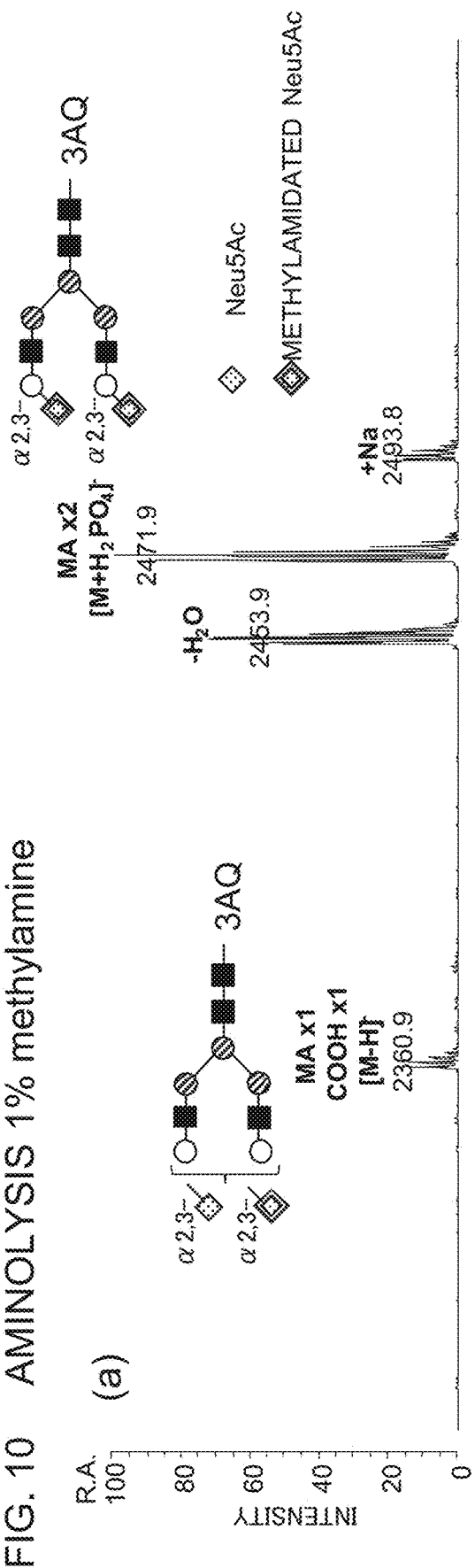
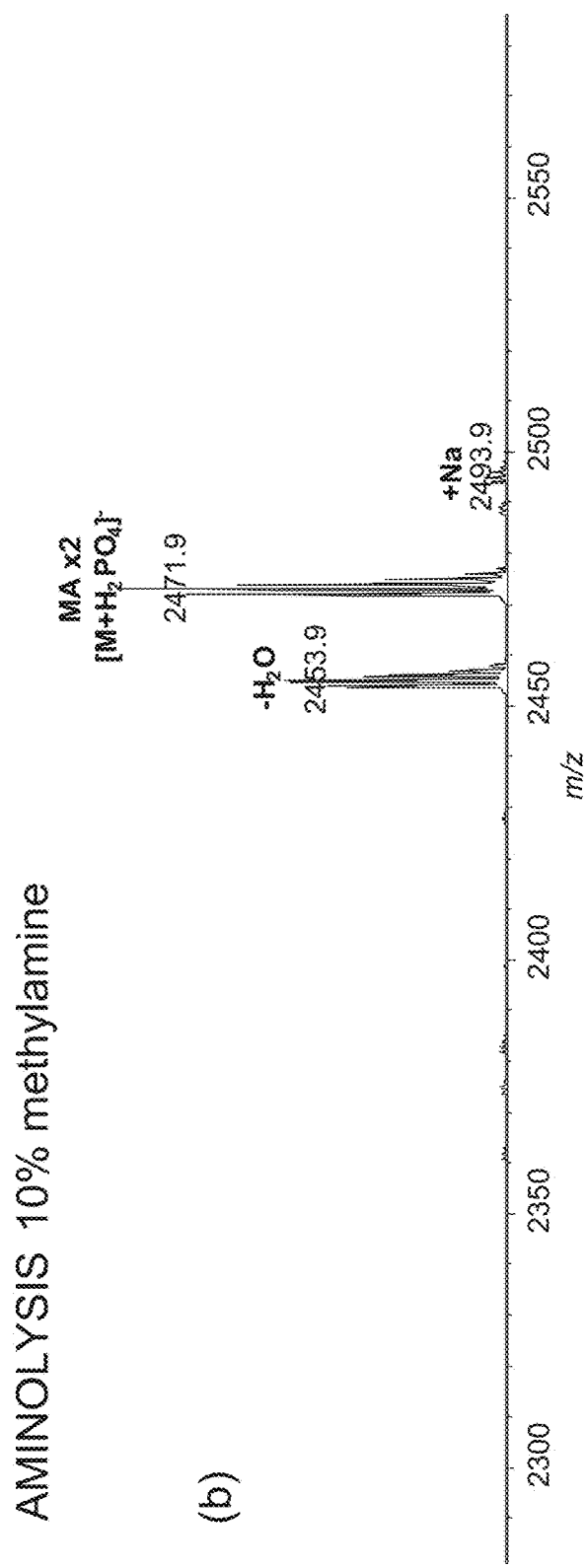
FIG. 10 (a) AMINOLYSIS 1% methylamine
(b) AMINOLYSIS 10% methylamine

METHOD FOR PREPARING ANALYTICAL SAMPLE, ANALYSIS METHOD, AND KIT FOR PREPARING ANALYTICAL SAMPLE

INCORPORATION BY REFERENCE

The disclosure of the following priority application is herein incorporated by reference: Japanese Patent Application No. 2018-157702 filed Aug. 24, 2018

TECHNICAL FIELD

The present invention relates to a method for preparing an analytical sample, an analysis method, and a kit for preparing an analytical sample.

BACKGROUND ART

Sialic acid is a saccharide abundant in the living body. Sialic acid is also included in glycans linked to protein in the living body, and is often present at a non-reducing end of a glycan. Thus, sialic acid is positioned in the outermost side of such a glycoprotein molecule, and plays an important role because it is directly recognized by other molecules. Sialic acids may have different linkage types to the adjacent saccharide. For example, α2,3- and α2,6-linkage types are primarily known for human N-linked glycans (N-glycans), and in addition to these linkage types, α2,8- and α2,9-linkage types are known for O-linked glycans (O-glycans) and glycosphingolipids. Sialic acids with such different linkage types are recognized by different molecules, and thus can play different roles.

Sialic acid can undergo various modifications such as acetylation, and formation of a sialic acid lactone is included therein. It has been known that lactone structures exist in ganglioside, which is a glycolipid, and milk oligosaccharide chains (see NPTL 1). Polysialic acid structures, which are highly expressed in the brain and include sialic acid of α2,8- or α2,9-linkage types, are said to be likely to undergo formation of a lactone structure. In addition, biopharmaceutical products, in particular, glycans of antibody drugs are reported to include lactone structures. NPTL 2 discloses that a certain biosimilar drug includes a lactone structure.

Methods for distinguishing between sialic acid including a lactone structure and sialic acid including no lactone structure for quantitative detection of them have not been established yet. Since sialic acid including a lactone structure is smaller than sialic acid including no lactone structure by the size of one water molecule ($H_2O$), they can be distinguished from each other by using mass spectrometry. However, lactone structures are extremely unstable, and easily hydrolyzed even in water, and more quickly hydrolyzed under acidic or basic conditions. Therefore, particularly when a glycan is enzymatically or chemically cleaved into a free glycan for analysis, and when a glycan is converted into glycopeptides by protease digestion for analysis, for example, successful completion of quantitative analysis of lactone structures is not guaranteed because of their decomposition.

In mass spectrometry and the like for a glycan including sialic acid, derivatization of sialic acid is performed as a pretreatment for the glycan. This leads to overcoming of disadvantages such as suppression of ionization and elimination of sialic acid through neutralization of the carboxy group, having negative charge, of sialic acid by esterification, amidation, or the like. As a further evolution of this method, a method of quantifying sialic acids in a linkage-specific manner has been proposed (see PTL 1 and NPTL 3). However, this approach is incapable of distinguishing sialic acid originally present as lactone structures from normal sialic acid differing therefrom.

In NPTL 4, lactones in gangliosides are detected through mass spectrometry after ammonolysis and permethylation. However, a limitation is that all of the hydroxy groups of a glycan are methylated through the permethylation.

CITATION LIST

Patent Literature

PTL 1: JP 6135710 B

Non-Patent Literature

NPTL 1: Riboni L, Sonnino S, Acquotti D, Malesci A, Ghidoni R, Egge H, Mingrino S, Tettamanti G. "Natural occurrence of ganglioside lactones. Isolation and characterization of GD1b inner ester from adult human brain" Journal of Biochemical Chemistry, (US), American Society for Biochemistry and Molecular Biology, Jun. 25, 1986, Volume 261, Issue 18, pp. 8514-8519

NPTL 2: Liu S, Gao W, Wang Y, He Z, Feng X, Liu B F, Liu X. "Comprehensive N-Glycan Profiling of Cetuximab Biosimilar Candidate by NP-HPLC and MALDI-MS" PLoS One, (US), Public Library of Science, Jan. 10, 2017, Volume 12, Issue 1, e0170013

NPTL 3: Nishikaze T, Tsumoto H, Sekiya S, Iwamoto S, Miura Y, Tanaka K. "Differentiation of Sialyl Linkage Isomers by One-Pot Sialic Acid Derivatization for Mass Spectrometry-Based Glycan Profiling," Analytical Chemistry, (US), ACS Publications, Feb. 21, 2017, Volume 89, Issue 4, pp. 2353-2360

NPTL 4: Levery S B, Salyan M E K, Roberts C E, Bouchon B, Hakomori S. "Strategies for characterization of ganglioside inner esters I-Fast atom bombardment mass spectrometry" Biomedical & Environmental Mass Spectrometry, (UK), John Wiley & Sons, May, 1990, Volume 19, Issue 5, pp. 303-310

SUMMARY OF INVENTION

Technical Problem

Needed is a method for distinguishing sialic acid including a lactone structure and sialic acid including no lactone structure each originally contained in a sample for quantification of them with high accuracy.

Solution to Problem

According to the 1st aspect of the present invention, a method for preparing an analytical sample for analysis of a glycan that includes a lactone structure and is contained in a sample comprises: performing a first amidation reaction that amidates a sialic acid including the lactone structure through addition of a first amidation reaction solution to the sample, the first amidation reaction solution containing ammonia, an amine, or a salt thereof as a first nucleophilic agent that is reacted with the sialic acid including the lactone structure; and performing a second reaction that modifies at least a part of sialic acids not amidated in the first amidation reaction through a method different from permethylation.

According to the 2nd aspect of the present invention, in the method for preparing an analytical sample according to the 1st aspect, it is preferred that a time during which the sample is in contact with the first amidation reaction solution in order to perform the first amidation reaction is shorter than 30 minutes.

According to the 3rd aspect of the present invention, in the method for preparing an analytical sample according to the 1st or 2nd aspect, it is preferred that the first amidation reaction solution does not include a dehydration condensation agent that is reacted with the sialic acid.

According to the 4th aspect of the present invention, in the method for preparing an analytical sample according to any one of the 1st to 3rd aspects, it is preferred that the amine is a primary amine.

According to the 5th aspect of the present invention, in the method for preparing an analytical sample according to any one of the 1st to 4th aspects, it is preferred that the amine includes an alkyl group.

According to the 6th aspect of the present invention, in the method for preparing an analytical sample according to 5th aspect, it is preferred that the alkyl group is unbranched.

According to the 7th aspect of the present invention, in the method for preparing an analytical sample according to any one of the 1st to 6th aspects, it is preferred that pH of the first amidation reaction solution is 8.0 or higher.

According to the 8th aspect of the present invention, in the method for preparing an analytical sample according to any one of the 1st to 7th aspects, it is preferred that the first amidation reaction solution contains an amine or a salt thereof, and a concentration of the amine or salt thereof is 0.5 M or more.

According to the 9th aspect of the present invention, in the method for preparing an analytical sample according to any one of the 1st to 8th aspects, it is preferred that the second reaction is performed in a state in which the sample is bonded to or adsorbed on a solid phase carrier.

According to the 10th aspect of the present invention, in the method for preparing an analytical sample according to any one of the 1st to 9th aspects, it is preferred that the sample subjected to the first amidation reaction is contacted with a second reaction solution in the second reaction, the second reaction solution contains ammonia, an amine, an alcohol, or a salt thereof as a second nucleophilic agent that is reacted with a sialic acid not amidated in the first amidation reaction, at least a part of sialic acids that does not include the lactone structure and is contained in the sample before the first amidation reaction is amidated or esterified through the second reaction, and the first nucleophilic agent and the second nucleophilic agent are different.

According to the 11th aspect of the present invention, in the method for preparing an analytical sample according to 10th aspect, it is preferred that the second reaction solution contains a dehydration condensation agent.

According to the 12th aspect of the present invention, in the method for preparing an analytical sample according to any one of the 1st to 9th aspects, it is preferred that the sample subjected to the first amidation reaction is contacted with a second reaction solution in the second reaction, and the second reaction solution contains an alkylating agent for ester synthesis.

According to the 13th aspect of the present invention, in the method for preparing an analytical sample according to any one of the 1st to 11th aspects, it is preferred that at least a part of the sialic acids is modified based on a linkage type of the sialic acid in the second reaction.

According to the 14th aspect of the present invention, in the method for preparing an analytical sample according to 13th aspect, it is preferred that $\alpha 2,6$-sialic acid and at least one of $\alpha 2,3$-sialic acid, $\alpha 2,8$-sialic acid and $\alpha 2,9$-sialic acid are modified into different modified products in the second reaction.

According to the 15th aspect of the present invention, an analysis method comprises: preparing an analytical sample by using the method for preparing an analytical sample according to any one of the 1st to 14th aspects; and analyzing the prepared analytical sample.

According to the 16th aspect of the present invention, in the method for preparing an analytical sample according to 15th aspect, it is preferred that the prepared analytical sample is analyzed through at least one of mass spectrometry and chromatography.

According to the 17th aspect of the present invention, a kit for preparing an analytical sample, the kit comprises: at least one of ammonia, an amine, and a salt thereof, wherein: the kit is used for the method for preparing an analytical sample according to any one of the 1st to 14th aspects.

Advantageous Effects of Invention

The present invention enables to distinguish sialic acid including a lactone structure and sialic acid including no lactone structure each originally contained in a sample for quantification of them with high accuracy.

BRIEF DESCRIPTION OF DRAWINGS

FIG. 3A shows a conceptual diagram illustrating a structure of a glycan contained in a sample used in Examples.

FIG. 3B shows a conceptual diagram illustrating a structure of a glycan contained in a sample used in Examples.

FIG. 3C shows a conceptual diagram illustrating a structure of a glycan contained in a sample used in Examples.

FIG. 10 shows mass spectra acquired in mass spectrometry in the negative ion mode for reaction products obtained through a lactonization reaction and aminolysis of a glycan released from α2,3-sialylglycopeptide, where (a) shows a mass spectrum with a methylamine concentration of 1% in the aminolysis, and (b) shows a mass spectrum with a methylamine concentration of 10% in the aminolysis.

DESCRIPTION OF EMBODIMENTS

Hereinafter, embodiments of the present invention will be described with reference to the drawings. Shown in the embodiments below are methods for preparing an analytical sample for analysis of a lactone in a glycan originally contained in a sample. The present inventor has found quantification of sialic acid including a lactone structure through amidation thereof by adding to a sample a reaction solution containing ammonia, amine, or a salt thereof that is reacted with sialic acid including a lactone structure.

First Embodiment

Figure 1:
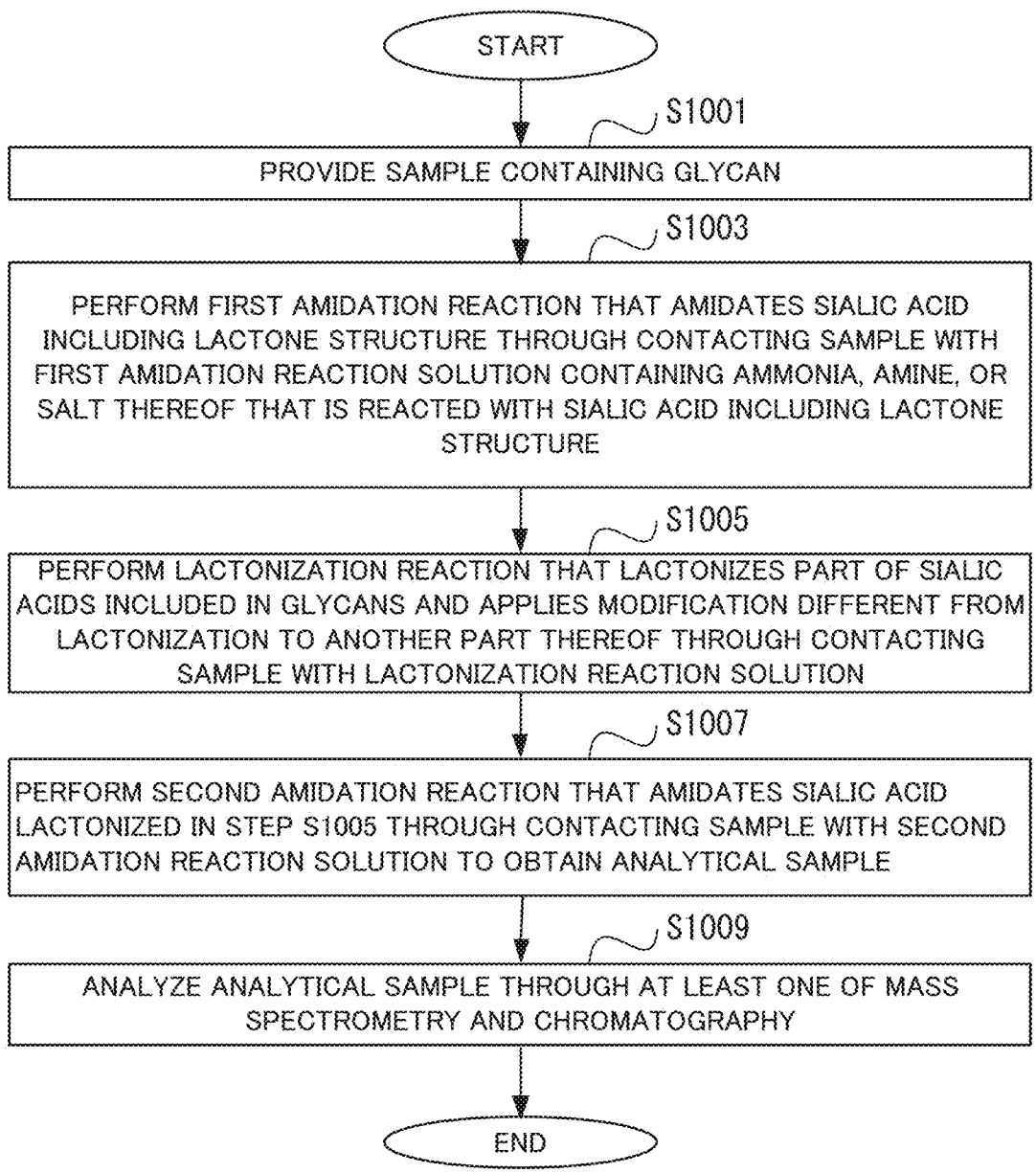
FIG. 1 shows a flowchart illustrating the procedure of an analysis method according to one embodiment.

FIG. 1 shows a flowchart illustrating the procedure of an analysis method related to the method for preparing an analytical sample (sample for analysis) in the present embodiment. This analysis method is for the purpose of analyzing a lactone in a glycan originally contained in a sample. A sample containing a glycan is provided in a step S1001.

The sample containing a glycan is not limited, and can contain at least one molecule selected from the group consisting of a free glycan, a glycopeptide and a glycoprotein, and a glycolipid. The method for preparing an analytical sample according to the present embodiment is used for modification of sialic acid that includes a lactone structure and is contained in a glycan, and further, suitably used for analysis of the linkage type of sialic acid. Hence, it is preferable for the sample to contain a glycan which may have sialic acid at an end such as a N-linked glycan, an O-linked glycan, and a glycolipid-type glycan. The glycan in the sample more preferably contains at least one of α2,3-sialic acid, α2,8-sialic acid, and α2,9-sialic acid, and α2,6-sialic acid, but is not limited to glycans containing them.

The completion of the step S1001 is followed by a step S1003.

First Amidation Reaction

In the step S1003, a first amidation reaction is performed that amidates the sialic acid including a lactone structure originally contained in the sample through contacting the sample with a reaction solution for amidation of sialic acid including a lactone structure (hereinafter, referred to as "first amidation reaction solution"). The present inventor has found a method for directly and quickly amidating a lactone, which is quite contrast to the common general knowledge, namely, ring-opening of a lactone through hydrolysis followed by amidation of the carboxy group. This reaction is different from hydrolysis since the reaction suitably proceeds even under anhydrous conditions, and inferred to be aminolysis based on the interaction between an amino group and a lactone. Hereinafter, ring-opening and amidation of a lactone with ammonia, amine, or a salt thereof, available even under anhydrous conditions, is referred to as "aminolysis." A lactone or a lactone structure originally contained in the sample are referred to as, for example, a lactone or a lactone structure to be analyzed, as appropriate. This aminolysis reaction needs substantially no dehydration condensation agent, and hence only lactonized sialic acid can be selectively amidated without affecting normal sialic acid not forming a lactone structure.

Not only a lactone structure formed between sialic acid and a monosaccharide adjacent to the sialic acid, but also, for example, a lactone structure formed inside of sialic acid may be regarded as a lactone structure of sialic acid to be analyzed.

An operation to remove the first amidation reaction solution from the sample after the first amidation reaction is performed. The operation to remove the first amidation reaction solution is not limited and any operation which sufficiently lowers the concentrations of reagents necessary for the first amidation reaction can be used as appropriate, and examples thereof include separating the first amidation reaction solution from the glycan bonded to the solid phase carrier through centrifugation or the like and then washing with a washing solution; and evaporation of the sample to dryness through centrifugal concentration under reduced pressure.

The first amidation reaction solution contains ammonia, an amine or a salt thereof. It is preferable so as not to allow sialic acid not lactonized originally in the sample to be lactonized by accident that the first amidation reaction solution be free of or substantially free of a dehydration condensation agent. Or it is preferable that the first amidation reaction solution contain only a sufficiently low concentration of a dehydration condensation agent such that such undesired lactonization is not caused. The first amidation reaction is preferably performed only through contacting the sample with the first amidation reaction solution, and the lactone to be analyzed is stabilized through such a simple operation.

Amine in First Amidation Reaction

If the amine is used in the first amidation reaction, the amine contained in the first amidation reaction solution is preferably a primary amine, more preferably a primary amine having a linear hydrocarbon group, and even more preferably a primary amine having a linear alkyl group. The primary amine having a linear alkyl group as the amine contained in the first amidation reaction solution is preferably a primary amine having 10 or less carbon atoms, more preferably a primary amine having seven or less carbon atoms, even more preferably methylamine, ethylamine, propylamine, butylamine, or pentylamine, and the most preferably methylamine. It is preferable for the amine contained in the first amidation reaction solution to have a linear structure without any branch (hereinafter, "branch" refers to a branch of a hydrocarbon chain), or have a smaller number of carbon atoms, because the lactone to be analyzed is more efficiently amidated.

If the amine contained in the first amidation reaction solution is a primary amine having an unsaturated linear hydrocarbon group, the unsaturated linear hydrocarbon group preferably includes a double bond, and more preferably includes an allyl group, and the amine is the most preferably allylamine. The amine contained in the first amidation reaction solution may be a primary amine including a hydroxy group, and in this case the amine is preferably ethanolamine. The amine contained in the first amidation reaction solution is not limited thereto, and may include various functional groups other than alkyl groups. When a glycan is modified and provided with such a functional group as a result of the first amidation reaction, the modified glycan can be separated more easily not only through mass spectrometry but also through chromatography or the like.

The first amidation reaction solution may contain a salt of any of the above amine.

Concentration of First Amidation Reaction Solution

The concentration of ammonia, amine, or a salt thereof in the first amidation reaction solution is preferably 0.1 M (M denotes mol/L) or more, more preferably 0.3 M or more, even more preferably 0.5 M or more, further preferably 1.0 M or more, and the most preferably 3.0 M or more. In a preferred example, the first amidation reaction solution contains ammonia or a primary amine, in particular, methylamine, and the concentration of the ammonia or primary amine such as methylamine is preferably 0.1 M or more, more preferably 0.3 M or more, even more preferably 0.5 M or more, further preferably 1.0 M or more, and the most preferably 3.0 M or more. The higher the concentration of the amine or the like in the first amidation reaction solution is, the more reliably the lactone to be analyzed can be amidated.

Solvent of First Amidation Reaction Solution

The solvent of the first amidation reaction solution may be an aqueous solvent or an organic solvent. The water content of the solvent is appropriately controlled in order to prevent hydrolysis of the lactone to be analyzed and reliably cause quick amidation, and a dehydrated solvent, which has been subjected to a dehydration operation to reduce the water content, and an anhydrous solvent can be used. The solvent of the first amidation reaction solution preferably contains at least one of methanol and acetonitrile (ACN).

The first amidation reaction solution may contain a significant amount of water ($H_2O$), and the solvent of the first amidation reaction solution may be water.

pH of First Amidation Reaction Solution

The pH of the first amidation reaction solution is preferably 7.7 or higher, more preferably 8.0 or higher, even more preferably 8.8 or higher, and the most preferably 10.3 or higher. Higher pH is preferred for the first amidation reaction solution because the lactone to be analyzed is more reliably amidated.

Time Needed for First Amidation Reaction

The first amidation reaction is completed within several seconds to several minutes. Thus, the time during which the sample is in contact with the first amidation reaction solution for the first amidation reaction of the lactone (hereinafter, referred to as "reaction time") is preferably shorter than 1 hour, more preferably shorter than 30 minutes, even more preferably shorter than 15 minutes, further preferably shorter than κ minutes, and the most preferably shorter than 1 minute. It is suitable to wash the sample with the first amidation reaction solution, or only to temporarily pass the first amidation reaction solution through the sample held on a carrier or the like. The sample may be mixed with the first amidation reaction solution and directly subjected to evaporation to dryness without spending any reaction time. Since the first amidation reaction is completed within a short time in this way, deterioration of the quantitativity due to the decomposition of the lactone, which is unstable, can be prevented in analysis of the glycan. Through setting the reaction time of the first amidation reaction short, analysis of the sample becomes more efficient.

Phase for First Amidation Reaction

The state of the sample in causing the first amidation reaction is not limited, as long as the state allows the sample to contact with the first amidation reaction solution. However, it is preferable to perform the first amidation reaction in a liquid phase because if the first amidation reaction is performed in a solid phase, the accuracy of quantification of the lactone to be analyzed is lowered by lactonization of sialic acid during an immobilization reaction.

If the sample contains a glycoprotein, a glycopeptide, or a glycolipid, the glycan may be released from a glycoprotein, a glycopeptide, or a glycolipid after the first amidation reaction. As the method for releasing a glycan, enzymatic treatment with an enzyme such as N-glycosidase, O-glycosidase, or endoglycoceramidase, hydrazinolysis, or β-elimination by alkali treatment, or the like can be used. In releasing a N-linked glycan from the peptide chain of glycopeptide or glycoprotein, enzyme treatment is suitably used, for example, with peptide-N-glycosidase F (PNGase F), peptide-N-glycosidase A (PNGase A), or endo-β-N-acetylglucosaminidase (Endo M). Alternatively, modification such as pyridylamination (PA labeling) can be appropriately performed for a reducing end of the glycan.

If the sample contains a glycopeptide or a glycoprotein, treatment to suppress a side reaction of the peptide moiety can be appropriately performed after the first amidation reaction, as described later in the section "Suppression of Side Reaction of Glycopeptide and Glycoprotein". In the case that the peptide chain of a glycopeptide or a glycoprotein includes a large number of amino acid residues, it is preferable to cleave the peptide chain in use, for example, through enzymatic cleavage. In preparing a sample for mass spectrometry, for example, the number of amino acid resides in the peptide chain is preferably 30 or less, more preferably 20 or less, and even more preferably 15 or less. In the case that the origin of peptide to which a glycan is linked is needed to be clarified, the number of amino acid resides in the peptide chain is preferably two or more, and more preferably three or more.

A digestive enzyme is used in cleaving the peptide chain of a glycopeptide or a glycoprotein, and examples thereof include trypsin, Lys-C, arginine endopeptidase, chymotrypsin, pepsin, thermolysin, proteinase K, and pronase E. Two or more of these digestive enzymes may be used in combination. Conditions for cleavage of the peptide chain are not limited, and a protocol suitable for the digestive enzyme to be used is appropriately employed. Before the cleavage, denaturation treatment or alkylation treatment may be performed for the protein or peptide in the sample. Conditions for the denaturation treatment or alkylation treatment are not limited. The cleavage of the peptide chain may be achieved not through enzymatic cleavage but through chemical cleavage or any other method. The above-described treatment for release of a glycan, suppression of a side reaction, or cleavage of peptide may be performed before the first amidation reaction as long as the lactone to be analyzed can be quantified with a desired accuracy.

The completion of the step S1003 is followed by a step S1005.

In the step S1003, the lactone to be analyzed was amidated to be stabilized. In the method for preparing an analytical sample and analysis method in the present embodiment, sialic acid not amidated in the step S1003 is modified in a linkage-specific manner, and analyzed with distinguishing from sialic acid including the lactone to be analyzed.

Lactonization Reaction

In the step S1005, a lactonization reaction is performed (hereinafter, the expression "lactonization reaction" refers to the lactonization reaction in step S1005, unless otherwise stated) that lactonizes at least a part of sialic acids included in the glycan through contacting the sample with a reaction solution for lactonization (hereinafter, referred to as "lactonization reaction solution"). In the lactonization reaction, a part of sialic acids not lactonized is subjected to modification differing from lactonization. In the lactonization reaction, $\alpha 2,3$-sialic acid, $\alpha 2,8$-sialic acid, and $\alpha 2,9$-sialic acid are suitably lactonized.

The lactonization reaction solution contains a dehydration condensation agent and a nucleophilic agent containing an alcohol, an amine, or a salt thereof. The types and concentrations of the dehydration condensation agent and nucleophilic agent are adjusted to selectively cause a dehydration reaction or a nucleophilic reaction based on the linkage type of sialic acid.

The lactone generated through intramolecular dehydration of the carboxy group of $\alpha 2,3$-sialic acid is a 6-membered ring, and the lactone generated through intramolecular dehydration of the carboxy group of $\alpha 2,6$-sialic acid is a 7-membered ring. Six-membered rings are more stable than 7-membered rings, and thus $\alpha 2,3$-sialic acid, which generates a 6-membered ring, has a higher tendency to be lactonized than $\alpha 2,6$-sialic acid. The carboxy group of $\alpha 2,3$-sialic acid is present at a position causing relatively high steric hindrance as compared with the carboxy group of $\alpha 2,6$-sialic acid, and hence $\alpha 2,3$-sialic acid is less reactive with large molecules than $\alpha 2,6$-sialic acid. Based on such difference in molecular structure among the linkage types of sialic acid, the types and concentrations of the dehydration condensation agent and nucleophilic agent are adjusted to provide different modifications for different linkage types of sialic acids.

The nucleophilic agent contained in the lactonization reaction solution (hereinafter, referred to as "second nucleophilic agent") is different from the nucleophilic agent contained in the first amidation reaction solution (hereinafter, referred to as "first nucleophilic agent"). When an analytical sample obtained by using the method for preparing an analytical sample in the present embodiment is analyzed through mass spectrometry, the first nucleophilic agent and the second nucleophilic agent are selected so that they are different in mass. When an analytical sample obtained by using the method for preparing an analytical sample in the present embodiment is analyzed through chromatography, it is preferable for easy separation of the first nucleophilic agent and the second nucleophilic agent through chromatography that they have different substituent groups.

Dehydration Condensation Agent in Lactonization Reaction

It is preferable for the dehydration condensation agent to contain a carbodiimide. This is because when a carbodiimide is used, the carboxy group present at a site causing high steric hindrance is less likely to be amidated than in use of a phosphonium-based dehydration condensation agent (what is called BOP reagent) or an uronium-based dehydration condensation agent as the dehydration condensation agent. Examples of the carbodiimide include N,N'-dicyclohexylcarbodiimide (DCC), N-(3-dimethylaminopropyl)-N'-ethylcarbodiimide (EDC), N,N'-diisopropylcarbodiimide (DIC), 1-tert-butyl-3-ethylcarbodiimide (BEC), N,N'-di-tert-butylcarbodiimide, 1,3-di-p-toluylcarbodiimide, bis(2,6-diisopropylphenyl)carbodiimide, bis(trimethylsilyl)carbodiimide, and 1,3-bis(2,2-dimethyl-1,3-dioxolan-4-ylmethyl) carbodiimide(BDDC), and salts thereof.

Additive in Lactonization Reaction

To promote dehydration condensation by the dehydration condensation agent and suppress a side reaction, a highly nucleophilic additive is preferably used in addition to the carbodiimide. The highly nucleophilic additive for use is, for example, 1-hydroxybenzotriazole (HOBt), 1-hydroxy-7-aza-benzotriazole (HOAt), 4-(dimethylamino)pyridine (DMAP), ethyl 2-cyano-2-(hydroxyimino)acetate (Oxyma), N-hydroxy-succinimide (HOSu), 6-chloro-1-hydroxy-benzotriazole (Cl-HOBt), or N-hydroxy-3,4-dihydro-4-oxo-1,2,3-benzotriazine (HOOBt).

Nucleophilic Agent in Lactonization Reaction (Second Nucleophilic Agent)

The amine for use as the second nucleophilic agent preferably contains a primary or secondary alkylamine having two or more carbon atoms. The primary alkylamine is preferably, for example, ethylamine, propylamine, isopropylamine, butylamine, sec-butylamine, or tert-butylamine. The secondary alkylamine is preferably, for example, dimethylamine, ethylmethylamine, diethylamine, propylmethylamine, or isopropylmethylamine. To lower the probability of the occurrence of amidation of the carboxy group present at a site with high steric hindrance such as the carboxy group of $\alpha 2,3$-sialic acid, use of an amine having a branched alkyl group such as isopropylamine is preferred. If an amine is used as the nucleophilic agent in the lactonization reaction solution, the carboxy group of a part of sialic acids such as $\alpha 2,6$-sialic acid is amidated based on the linkage type of the sialic acid.

The alcohol for use as the second nucleophilic agent is not limited, and methanol, ethanol, or the like can be used. If an alcohol is used as the nucleophilic agent in the lactonization reaction solution, the carboxy group of a part of sialic acids such as $\alpha 2,6$-sialic acid is esterified based on the linkage type of the sialic acid.

The second nucleophilic agent may contain a salt of any of the above nucleophilic agents.

Concentrations of Dehydration Condensation Agent and Amine

The concentration of the dehydration condensation agent in the lactonization reaction solution is, for example, preferably 1 mM to 5 M, and more preferably 10 mM to 3 M. If a carbodiimide and a highly nucleophilic additive such as HOAt and HOBt are used in combination, the concentration of each is preferably in the above range. The concentration of the amine in the lactonization reaction solution is preferably 0.01 to 20 M, and more preferably 0.1 M to 10 M. The reaction temperature during the lactonization reaction is preferably around $-20°$ C. to $100°$ C., and more preferably $-10°$ C. to $50°$ C.

Phase for Lactonization Reaction

The lactonization reaction can be performed in any of a liquid phase and a solid phase. The state of the sample in causing the lactonization reaction is not limited as long as the state allows the sample to contact the lactonization reaction solution. However, it is preferable to contact the sample with the lactonization reaction solution in a state in which glycans contained in the sample subjected to the first amidation reaction are bonded to or adsorbed on a solid phase carrier.

If the reaction is performed in a solid phase, the solid phase carrier to be used is not limited as long as the solid phase carrier is capable of immobilizing a glycan, a glycopeptide, a glycoprotein, or the like. To immobilize a glycopeptide or a glycoprotein, for example, a solid phase carrier having, as a ligand, an epoxy group, a tosyl group, a carboxy group, an amino group, or the like can be used. To immobilize a glycan, for example, a solid phase carrier having, as a ligand, a hydrazide group or an aminooxy group can be used. It is also preferable to allow a glycan to be adsorbed on a carrier, in other words, a stationary phase for hydrophilic interaction chromatography (hereinafter referred to as "HILIC"), and it is more preferable that the carrier for HILIC include an amide group.

Reacting in a state in which the sample is immobilized to a solid phase carrier facilitates removal of the reaction solution and desalting and purification, and sample preparation can be simplified. In use of a solid phase carrier, the sample is immobilized as the form of glycoprotein or glycopeptide, and after the lactonization reaction, the sample is cleaved with, for example, glycosidase such as PNGase F. Thereby, the sample after the lactonization reaction can be collected as a free glycan.

As necessary, the sample after the lactonization reaction may be subjected to treatment such as purification, desalting, solubilization, concentration, or drying by using a known method or the like. The same applies before and after the second amidation reaction described later.

Conditions described later for the second amidation reaction can be employed for release of the sample from the solid phase carrier. Reacting in a state in which the sample is immobilized to a solid phase carrier facilitates, for example, removal of the lactonization reaction solution after the lactonization reaction, and sialic acid can be efficiently modified.

The completion of the step S1005 is followed by a step S1007.

Second Amidation Reaction

In the step S1007, the second amidation reaction is performed, in which the sample is contacted with a reaction solution (hereinafter, referred to as "second amidation reaction solution") to amidate the sialic acid lactonized in step S1005, to obtain an analytical sample.

The composition and pH of the second amidation reaction solution and the reaction time are selected from the conditions for the first amidation reaction.

Although no dehydration condensation agent is needed for the second amidation reaction, a dehydration condensation agent may be contained in the second amidation reaction solution. For example, the second amidation reaction solution may be prepared by adding ammonia, an amine, or a salt thereof without removing the lactonization reaction solution added to the sample in step S1005. Thus, the second amidation reaction can stabilize the formed lactone, with a simple operation.

The nucleophilic agent contained in the second amidation reaction solution (referred to as "third nucleophilic agent") is different from both of the above-described first nucleophilic agent and second nucleophilic agent. When an analytical sample obtained by using the method for preparing an analytical sample in the present embodiment is analyzed through mass spectrometry, the first nucleophilic agent, the second nucleophilic agent, and the third nucleophilic agent are selected so that they are all different in mass. The first nucleophilic agent, the second nucleophilic agent, and the third nucleophilic agent are selected according to mass resolution of mass spectrometry so that accurate mass separation is achieved for an obtained modified product. The first nucleophilic agent, the second nucleophilic agent, and the third nucleophilic agent may be different substances, or identical substances to which different masses have been imparted by using stable isotopes. Alternatively, isobaric tags as represented by iTRAQ may be used. In this case, such tags are designed so that product ions obtained through cleavage performed between a first stage mass spectrometry and a second stage mass spectrometry have different values of m/z, and hence identification of the linkage types and lactone forms of sialic acids can be performed by using tandem mass spectrometry (MS/MS). Thus, in subjecting respective modified products modified with the first nucleophilic agent, the second nucleophilic agent, and the third nucleophilic agent to mass spectrometry in two or more stages, the modified products need to be separated in any of the stage by different values of m/z. When an analytical sample obtained by using the method for preparing an analytical sample in the present embodiment is analyzed through chromatography, it is preferable for easy separation of the first nucleophilic agent, the second nucleophilic agent, and the third nucleophilic agent through chromatography that they have different substituent groups.

Phase for Second Amidation Reaction

The second amidation reaction can be performed in any of a liquid phase and a solid phase. If the second amidation reaction is performed in a state in which the sample is immobilized to a solid phase, the second amidation reaction may be performed while the state in which the sample subjected to the lactonization reaction is immobilized to a solid phase is maintained. Alternatively, the sample after being subjected to the lactonization reaction may be immobilized to a solid phase to perform the second amidation reaction.

If the second amidation reaction is performed in a solid phase, any of the solid phase carriers described above for the lactonization reaction can be used. For immobilizing the sample to a solid phase carrier, the conditions described above for the lactonization reaction can be used. If the second amidation reaction is performed in a solid phase, after the sample immobilized to the solid phase carrier is subjected to action of the second amidation reaction solution for amidation, the sample can be suitably released and collected from a carrier, for example, through a chemical technique or an enzyme reaction. For example, a glycoprotein or a glycopeptide immobilized to the carrier may be enzymatically cleaved and collected by using glycosidase such as PNGase F or a digestive enzyme such as trypsin, or a glycan bonding to a solid phase carrier having a hydrazide group may be released and collected by using a weakly acidic solution. In HILIC, the sample can be subjected to the second amidation reaction with a second amidation reaction solution containing acetonitrile or the like as a solvent followed by elution with an aqueous solution such as water.

Through the above-described preparation method, sialic acid that includes a lactone structure originally contained in the sample is modified with the first nucleophilic agent in the first amidation reaction. Sialic acid that is of a linkage type less likely to be lactonized, such as α2,6-sialic acid, is modified with the second nucleophilic agent in the lactonization reaction. Sialic acids that are of linkage types likely to be lactonized, such as α2,3-, α2,8-, and α2,9-sialic acids, and originally include no lactone structure in the sample are lactonized in the lactonization reaction, and modified with the third nucleophilic agent in the second amidation reaction.

The completion of the step S1007 is followed by a step S1009.

In the step S1009, the sample is analyzed through at least one of mass spectrometry and chromatography. Through the above-described first amidation reaction, lactonization reaction, and second amidation reaction, glycans subjected to modification other than lactonization in the reactions have different masses respectively. Accordingly, these glycans can be separated through mass spectrometry on the basis of the presence or absence of a lactone structure to be analyzed and the linkage type of sialic acid.

The ionization method in the mass spectrometry is not limited, and matrix-assisted laser desorption/ionization (MALDI), electrospray ionization (ESI), nano-electrospray ionization (nano-ESI), or the like can be used. MALDI is particularly preferred for the ionization method. In ionization in the mass spectrometry, any of the positive ion mode and the negative ion mode may be used. The mass spectrometry may be performed in multiple stages, which allows suitable analysis of the structure of a glycan in addition to the linkage type of sialic acid, or the structure of a peptide chain.

If analysis is performed through chromatography, liquid chromatography is preferable. The column for liquid chromatography is not limited, and a hydrophobic reverse phase column such as C30, C18, C8, or C4, a carbon column, a normal phase column for HILIC, or any other column can be appropriately used. It is preferred that after liquid chromatography is performed, measurement is performed by mass spectrometry to precisely analyze components in the sample through multiple separation. In this case, it is more preferred that an eluate from a liquid chromatograph is directly ionized by, for example, ESI in a mass spectrometer under online control.

The data acquired through mass spectrometry or chromatography are analyzed, and, for example, quantification of sialic acid including a lactone structure originally contained in the sample is performed. For example, the intensity of glycans including sialic acid including a lactone structure to be analyzed, the proportion of glycans including sialic acid including a lactone structure to be analyzed among glycans including sialic acid, or the proportion of glycans including α2,3-sialic acid including a lactone structure to be analyzed among glycans including α2,3-sialic acid can be calculated. The same holds true for α2,8-sialic acid and α2,9-sialic acid. The method for analysing the data acquired through mass spectrometry or chromatography is not limited.

At the completion of the step S1009, the procedure is terminated.

Suppression of Side Reaction of Glycopeptide and Glycoprotein

In the case that the first amidation reaction solution, the lactonization reaction solution and the second amidation reaction solution are added to a glycopeptide or a glycoprotein to modify sialic acids as described above, a side reaction may occur, such as intramolecular dehydration condensation between an amino group and a carboxy group present in the side chain of an amino acid or at an end of the main chain in the glycopeptide or glycoprotein. In this case, the mass spectrum peak corresponding to a glycan to be analyzed is split, which disadvantageously complicates analysis.

The present inventor has revealed that the a side reaction of a peptide moiety is primarily derived from the presence of an amino group, and that preliminary blocking of amino groups, for example, by using chemical modification, before modification of sialic acids can suppress the side reaction of a peptide moiety in modification of sialic acids. For the details, see the following literature: Takashi Nishikaze, Sadanori Sekiya, Shinichi Iwamoto, Koichi Tanaka. "A Universal Approach to linkage-Specific Derivatization for Sialic Acids on Glycopeptides," Journal of The American Society for Mass Spectrometry, June, 2017, Volume 28, Issue 1 Supplement, Poster No. MP091. Modification with the lactonization reaction or the like according to the present embodiment can be similarly applied to a glycopeptide and a glycoprotein. For example, a glycopeptide or a glycoprotein is subjected to a reaction to block amino groups such as dimethylamidation and guanidinylation, and to the lactonization reaction and the second amidation reaction. If a method for forming lactone is then used according to the linkage type of sialic acid, the linkage type of sialic acid can be identified.

Some glycopeptides are less likely to undergo a side reaction by virtue of the properties based on the amino acid sequence. For example, a glycopeptide generated through digestion of the Fc region of IgG with a digestive enzyme such as trypsin does not include lysine, and the amino groups at the N-terminals quickly undergo cyclodehydration to be pyroglutamylated in the presence of a dehydration condensation agent. As a result, the amino groups are eliminated, and thus preliminary blocking of amino groups by dimethylamidation, guanidinylation or the like is unnecessary. For such glycopeptide, a mass spectrum sufficient for analysis can be acquired through the first amidation reaction, the lactonization reaction, and the second amidation reaction without blocking of amino groups.

Kit for Preparing Analytical Sample

A kit for preparing an analytical sample (hereinafter, referred to as "preparation kit") is provided which is suitable for use in the method for preparing an analytical sample according to the present embodiment. The contents of the preparation kit are not limited as long as a solution containing the first nucleophilic agent in the first amidation reaction is contained, and the kit can contain a regent and any consumable other than reagents for mass spectrometry. By using the preparation kit, an analytical sample can be more efficiently prepared.

Second Embodiment

The method for preparing an analytical sample in the second embodiment is performed in the same procedure as the method for preparing an analytical sample in the first embodiment, but the second embodiment is different from the first embodiment in that the sample subjected to the first amidation reaction is subjected to a reaction (hereinafter, referred to as "nonspecific modification reaction") to modify sialic acid without distinguishing the linkage type of sialic acid, in other words, nonspecifically to the linkage type of sialic acid.

Figure 2:
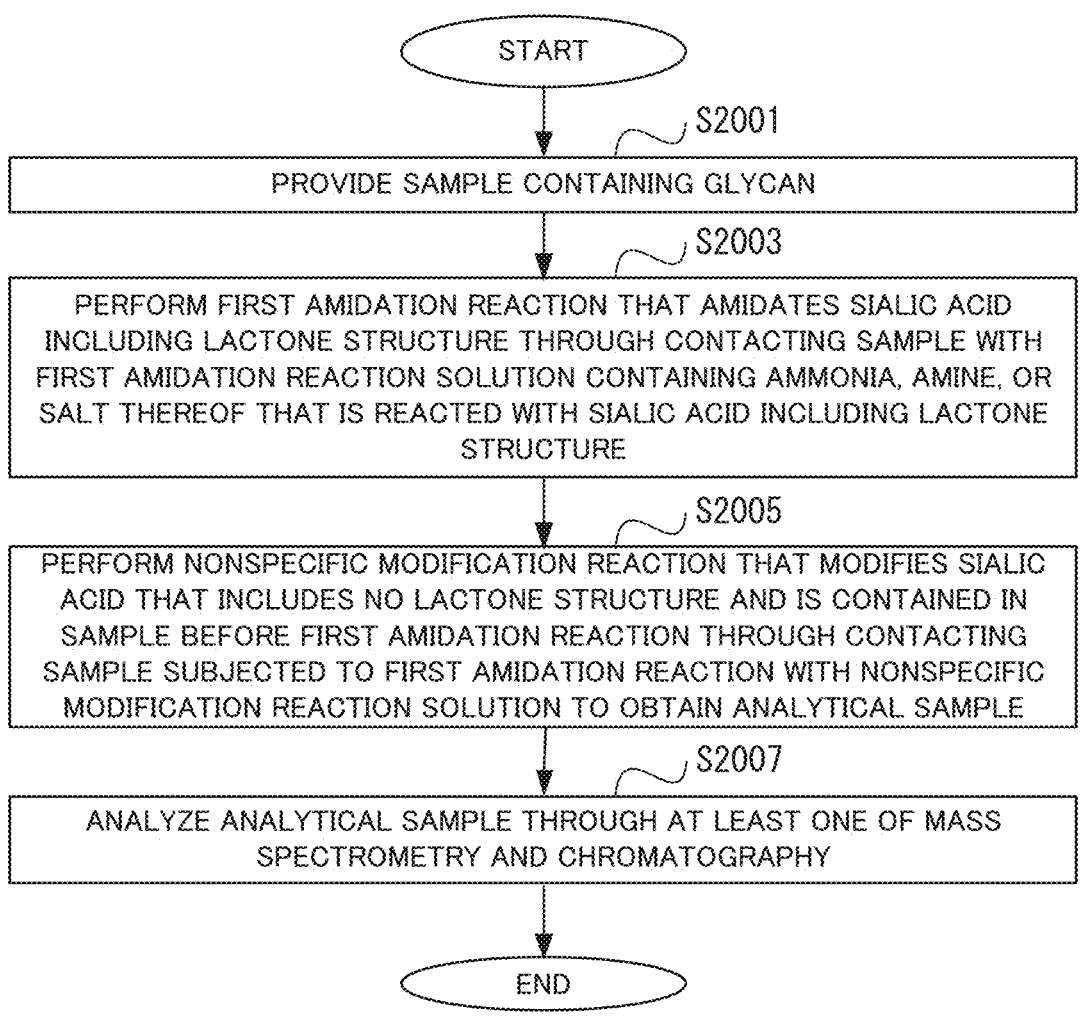
FIG. 2 shows a flowchart illustrating the procedure of an analysis method according to one embodiment.

FIG. 2 shows a flowchart illustrating the procedure of an analysis method related to the method for preparing an analytical sample in the present embodiment. Steps S2001 and S2003 are the same as steps S1001 and S1003 in the above-described embodiment, and hence description is omitted. The completion of the step S2003 is followed by a step S2005.

In the step S2005, the sample subjected to the first amidation reaction is contacted with a reaction solution for a nonspecific modification reaction (hereinafter, referred to as "nonspecific modification reaction solution") to perform the nonspecific modification reaction that modifies sialic acid that includes no lactone structure and is contained in the sample before the first amidation reaction. In the nonspecific modification reaction, sialic acid contained in the sample is modified irrespective of the linkage type of sialic acid, and an analytical sample is obtained.

The nonspecific modification reaction solution contains a dehydration condensation agent and a nucleophilic agent containing an alcohol, ammonia, an amine, or a salt thereof.

The nucleophilic agent contained in the nonspecific modification reaction solution (hereinafter, referred to as "fourth nucleophilic agent") is different from the first nucleophilic agent contained in the first amidation reaction solution. When an analytical sample obtained by using the method for preparing an analytical sample in the present embodiment is analyzed through mass spectrometry, the first nucleophilic agent and the fourth nucleophilic agent are selected so that they are different in mass. The first nucleophilic agent and the fourth nucleophilic agent are selected according to mass resolution of mass spectrometry so that accurate mass separation is achieved for an obtained modified product. As described above, the first nucleophilic agent and the fourth nucleophilic agent may be different substances, or identical substances to which different masses have been imparted by using stable isotopes or isobaric tags or the like. When an analytical sample obtained by using the method for preparing an analytical sample in the present embodiment is analyzed through chromatography, it is preferable for easy separation of the first nucleophilic agent and the fourth nucleophilic agent through chromatography that they have different substituent groups.

Dehydration Condensation Agent in Nonspecific Modification Reaction

It is preferable for the dehydration condensation agent to exhibit high reaction efficiency even for a carboxy group present at a site with high steric hindrance, and a phosphonium-based dehydration condensation agent or an uronium-based dehydration condensation agent is preferable.

Examples of phosphonium-based dehydration condensation agents include (benzotriazol-1-yloxy)tris-(dimethylamino)phosphonium (BOP), benzotriazol-1-yloxytris(pyrrolidino)phosphonium hexafluorophosphate (PyBOP), bromotris(dimethylamino)phosphonium hexafluorophosphate (BroP), bromotris(pyrrolidino)phosphonium hexafluorophosphate (PyBroP), (7-azabenzotriazol-1-yloxy)tris(pyrrolidino)phosphonium hexafluorophosphate (PyAOP), and chloro-tris-pyrrolidinophosphonium hexafluorophosphate (PyCloP). These are collectively referred to as "BOP reagents", and provide high reaction efficiency even for a carboxy group present at a site with high steric hindrance. Accordingly, they enable amidation with high reaction efficiency even for a site with high steric hindrance such as the carboxy group of α2,3-sialic acid.

Examples of uronium-based dehydration condensation agents include (1-cyano-2-ethoxy-2-oxoethylideneaminooxy)dimethylamino-morpholino-carbenium hexafluorophosphate (COMU), 2-(1H-benzotriazol-1-yl)-1,1,3,3 hexafluorophosphate (HBTU), 2-(7-azabenzotriazol-1-yl)-1,1,3,3 hexafluorophosphate (HATU), 2-(1H-benzotriazol-1-yl)-1,1,3,3-tetramethyluronium tetrafluoroborate (TBTU), 2-(5-norbornene-2,3-dicarboxyimide)-1,1,3,3-tetramethyluronium tetrafluoroborate (TNTU), and O-(N-succinimidyl)-1,1,3,3-tetramethyluronium tetrafluoroborate (TSTU). Among these uronium salts, COMU is particularly preferable.

Among the above dehydration condensation agents, phosphonium-based dehydration condensation agents are preferably used for enhanced amidation efficiency for lactones. In order to accelerate the reaction, it is desired to add a base such as N-methylmorpholine to a concentration of about 0.01 to 80% by weight based on the total of the reaction system. Addition of a base in the above-described concentration range to the reaction system can not only enhance the reaction efficiency but also prevent a side reaction or precipitation of reagents or the like. If N-methylmorpholine is contained as a base in the reaction system, the concentration is preferably 1 to 50% by weight. The conditions (including reaction temperature, reaction time or the like) for amidation are not limited, and, for example, known conditions for amidation of sialic acid can be directly applied.

Nucleophilic Agent in Lactonization Reaction (Fourth Nucleophilic Agent)

To enhance nucleophilic reaction efficiency, use of an amine having a small molecular volume as a nucleophilic agent is preferable since the carboxy group of α2,3-sialic acid is present at a site with high steric hindrance. Examples of preferable amines for the nonspecific modification reaction include primary alkylamines such as methylamine, ethylamine, propylamine, isopropylamine, butylamine, sec-butylamine, and tert-butylamine; and secondary alkylamines such as dimethylamine, ethylmethylamine, diethylamine, propylmethylamine, and isopropylmethylamine. The number of carbon atoms of alkylamine is preferably five or less, and more preferably three or less. Among the amines, primary alkylamines are preferable, primary linear alkylamines are more preferable, and methylamine and ethylamine are particularly preferable.

The nucleophilic agent for the nonspecific modification reaction is particularly preferably methylamine hydrochloride or ethylamine hydrochloride because of the high reactivity and less occurrence of a side reaction. Especially, use of methylamine hydrochloride or ethylamine hydrochloride in combination with PyAOP and N-methylmorpholine is more preferable.

If an alcohol is used as the nucleophilic agent, the alcohol is not limited, and methanol, ethanol, and the like can be used. If an alcohol is used as the nucleophilic agent in the nonspecific modification reaction solution, the carboxy group of sialic acid is esterified.

The fourth nucleophilic agent may contain a salt of any of the above-described nucleophilic agents. Alternatively, the nonspecific modification reaction may be performed without the dehydration condensation agent. For example, the carboxy group of sialic acid can be methylesterified through a reaction with iodomethane, an alkylating agent for ester synthesis, in a solution containing a solvent of DMSO. For the details, see an article by Powell et al. (Powell, A. K.; Harvey, D. J. Rapid Commun. Mass Spectrom. 1996, 10 (9), 1027-1032). As another example, methylesterification with an MTT reagent, an alkylating agent for ester synthesis, may be utilized. For the details, see a document by Miura et al. (Miura, Y.; Shinohara, Y.; Furukawa, J.; Nagahori, N.; Nishimura, S.-I. Chem. Eur. J. 2007, 13 (17), 4797-4804). The nonspecific modification reaction with such an alkylating agent for ester synthesis can be performed in any of a solid phase and a liquid phase.

Concentrations of Dehydration Condensation Agent and Amine

For example, the concentration of the dehydration condensation agent in the nonspecific modification reaction solution is preferably 1 mM to 5 M, and more preferably 10 mM to 3 M. The concentration of the amine in the nonspecific modification reaction solution is preferably 0.01 to 20 M, and more preferably 0.1 M to 10 M.

Phase for Nonspecific Modification Reaction

As with the case of the above-described lactonization reaction, the nonspecific modification reaction can be performed in any of a liquid phase and a solid phase.

If the nonspecific modification reaction is performed in a solid phase, any of the solid phase carriers described above for the lactonization reaction can be used. For immobilizing the sample to a solid phase carrier, the conditions described for the lactonization reaction can be used. For release of the sample from a solid phase carrier, the conditions described above for the second amidation reaction can be employed. Reacting in a state in which the sample is immobilized to a solid phase carrier facilitates, for example, removal of the nonspecific modification reaction solution after the nonspecific modification reaction and desalting and purification, and sialic acid can be efficiently modified.

Through the above-described preparation method, sialic acid including a lactone structure originally contained in the sample is modified with the first nucleophilic agent in the first amidation reaction. Sialic acid including no lactone structure originally contained in the sample is modified with the fourth nucleophilic agent in the nonspecific modification reaction.

The completion of the step S2005 is followed by a step S2007. The step 2007 is the same as step S1007 in the above-described embodiment, and hence description is omitted.

Although sialic acid including a lactone structure originally contained in the sample is amidated and the other sialic acid is then modified through amidation or esterification in the above-described first and second embodiments, the method is not particularly limited as long as sialic acid is modified through a method differing from permethylation. While all of the hydroxy groups in a glycan are methylated in permethylation, there is no such restriction in the present invention, and modification suitable for analysis to be conducted can be performed as appropriate.

The present invention is never limited to the contents of the above embodiments. Other modes contemplated from the scope of the technical idea of the present invention are also included in the scope of the present invention.

EXAMPLES

Hereinbelow, examples of the above embodiments will be described. However, the present invention is not limited to the following examples. Hereinafter, "%" denotes "% by weight" unless otherwise specified.

Preparation of Glycan Sample for Evaluation

To evaluate the methods for preparing an analytical sample in the above-described embodiments, a glycan sample containing sialic acid lactones with known concentrations was prepared. The prepared glycan sample contained the following LacA2, 33A2, and 66A2 in equal moles.

LacA2: A2-type glycan including two lactonized α2,3-sialic acids (A2 glycan)
33A2: A2 glycan including two non-lactonized α2,3-sialic acids
66A2: A2 glycan including two α2,6-sialic acids Structures of Glycan Samples FIG. 3A shows a conceptual diagram illustrating the structure of the glycan LacA2. LacA2 includes the basic structure consisting of N-acetyl-D-glucosamine (GlcNAc) and mannose (Man), and two side chains. To each of the two side chains, GlcNAc, galactose (Gal), and sialic acid (NeuNAc) are bonded. A lactone structure is formed at the bonding portion between an α2,3-sialic acid at a non-reducing end and a galactose to which the sialic acid is bonded, which is indicated by the double line B 1. To indicate that the linkage type of a sialic acid is α2,3-, the sialic acid is illustrated at the lower left of a galactose to which the sialic acid bonds.

FIG. 3B shows a conceptual diagram illustrating the structure of the glycan 33A2. Although 33A2 has a structure similar to LacA2, 33A2 differs from LacA2 in that no lactone structure is formed.

FIG. 3C shows a conceptual diagram illustrating the structure of the glycan 66A2. Although 66A2 has a structure similar to 33A2, 66A2 differs from 33A2 in that not α2,3-sialic acid but α2,6-sialic acid is present at each non-reducing end. To indicate that the linkage type of a sialic acid is α2,6-, the sialic acid is illustrated at the upper left of a galactose to which the sialic acid bonds.

Preparation of Glycans (A2 Glycans)

A2-type glycans were released from α2,3-sialylglycopeptide (SGP) and α2,6-SGP (FUSHIMI Pharmaceutical Co., Ltd.) by using PNGase F (Sigma-Aldrich Co. LLC). To each of tubes containing 20 μL of 1 nmol/μL α2,3-SGP and 20 μL of 1 nmol/μL α2,6-SGP, respectively, 10 μL of 0.25 U/μL PNGase F was added, and the tubes were subjected to tapping and centrifugation followed by overnight incubation at 37° C.

Each released glycan was desalted with a Stage Tip Carbon. A Stage Tip Carbon is a carbon column prepared by cutting an Empore Disk-Carbon (produced by 3M Company) into pieces having a diameter of approximately 1 mm and packing a 200 μL tip with the pieces. After 100 μL of ACN was added to a Stage Tip Carbon, the ACN was discharged through centrifugation. Thereafter, the same procedure was repeated with a 80% acetonitrile (ACN)/0.1% trifluoroacetic acid (TFA) solution and water in the order presented to wash and equilibrate the column carrier. Thereafter, the enzymatic reaction solution was added to the column, and the solution was discharged through centrifugation. Further, an operation in which 150 μL of a 0.1% TFA solution was added and then discharged through centrifugation was repeated three times for washing. Finally, an operation in which 20 μL of a 60% ACN/0.1% TFA solution was added and discharged through centrifugation was repeated twice for elution of the glycan. The eluents from the respective two operations were combined, and the resultant was subjected to evaporation to dryness to remove the solvent with a SpeedVac (Thermo Fisher Scientific). After the completion of evaporation to dryness, 200 μL of $H_2O$ was poured to each sample to redissolve it to 100 pmol/μL. A part of samples was diluted 10-fold to 10 pmol/μL.

Preparation of Equimolar Mixture of LacA2, 33A2, and 66A2

In a tube, 20 pmol of 33A2 was placed and subjected to evaporation to dryness, and 20 μL of a lactonization reaction solution containing isopropylamine (iPA) (2M iPA-HCl, 500 mM EDC-HCl, 500 mM HOBt, solvent: DMSO) for linkage-specific modification was added thereto, and reacted with stirring at 2000 rpm at room temperature for 1 hour. Under these conditions, 33A2 is completely lactonized. To the reaction solution, 120 μL of ACN was added for dilution to reach a total of 140 μL, which was used for amide purification.

Amide purification was performed as follows. To an amide tip (GL Sciences, Inc.), 100 μL of $H_2O$ was added, and then discharged through centrifugation. Thereafter, the same operation was performed with 90% ACN. Then, the above reaction solution diluted with ACN was added to the amide tip, and the solution was discharged through centrifugation. Further, an operation in which 150 μL of 90% ACN was added and then discharged through centrifugation was repeated twice for washing. Finally, an operation in which 20 μL of H$_2$O was added and discharged through centrifugation was repeated twice for elution of the glycan. The eluents from the respective two operations were combined, and the resultant was subjected to evaporation to dryness to remove the solvent with a SpeedVac.

The whole of the sample after the amide purification was transferred into a tube containing 33A2 and 66A2 each in 20 pmol. Thereby, a glycan sample for evaluation containing LacA2, 33A2, and 66A2 in generally equal moles was obtained, which was subject to evaporation to dryness with a SpeedVac.

Comparative Example 1

Modification of Sialic Acids

In Comparative Example 1, the linkage-specific amidation of sialic acids was performed without performing the first amidation. To the glycan sample for evaluation containing LacA2, 33A2, and 66A2 in equal moles, 20 μL of the above lactonization reaction solution was added, and the reaction was performed with stirring at 2000 rpm at room temperature for 1 hour. Thereafter, 20 μL of a 35% ethylamine aqueous solution as the second amidation reaction solution was added, and the resultant was stirred with a vortex mixer. Subsequently, 160 μL of an ACN solution containing TFA was added to the resulting reaction solution to reach a total of 200 μL, which was then subjected to amide purification.

Amide purification was performed as follows. To an amide tip (GL Sciences, Inc.), 100 μL of H$_2$O was added, and then discharged through centrifugation. Thereafter, the same operation was performed with a 90% ACN/0.1% TFA solution. Then, the above-described reaction solution diluted with the ACN solution containing TFA was added to the amide tip, and the solution was discharged through centrifugation. Further, an operation in which 150 μL of 90% ACN was added and then discharged through centrifugation was repeated twice for washing. Finally, an operation in which 20 μL of H$_2$O was added and discharged through centrifugation was repeated twice to elution of glycans. The eluents from the respective two operations were combined, and the resultant was subjected to evaporation to dryness to remove the solvent with a SpeedVac.

Next, the sample subjected to the amide purification was subjected to carbon purification. To a homemade Stage Tip Carbon, 50 μL of ACN was added, and then discharged through centrifugation. Thereafter, the same procedure was repeated with a 80% ACN/0.1% TFA solution and H$_2$O in the order presented to wash and equilibrate the column carrier. Then, the sample was redissolved in 20 μL of 0.1% TFA, and the resultant was added to the column, and the solution was discharged through centrifugation. Further, an operation in which 50 μL of a 0.1% TFA was added and then discharged through centrifugation was repeated three times for washing. Finally, an operation in which 10 μL of a 60% ACN/0.1% TFA solution was added and discharged through centrifugation was repeated twice for elution of glycans. The eluents from the respective two operations were combined, and the resultant was subjected to evaporation to dryness to remove the solvent with a SpeedVac.

Mass Spectrometry

The glycan subjected to evaporation to dryness was thoroughly redissolved in 10 μL of H$_2$O. Onto a μ focus plate (Hudson Surface Technology, Inc.) (hereinafter, simply referred to as the plate), 0.5 μL of the solution obtained through the redissolving was dropped. 0.5 μL of a solution obtained by dissolving 100 mM 3-aminoquinoline/p-coumaric acid (3AQ/CA) as a matrix and 2 mM ammonium dihydrogen phosphate (ADP) in 50% ACN was added, and the plate was placed on a heat block to react at 75° C. for 1.5 hours for labeling of reducing ends of glycans with 3AQ. After the completion of the reaction, the temperature of the plate was returned to room temperature, and time-of-flight mass spectrometry was performed through MALDI-QIT-TOF-MS (AXIMA-Resonance, Shimadzu/Kratos) in the negative ion mode.

Figure 4:
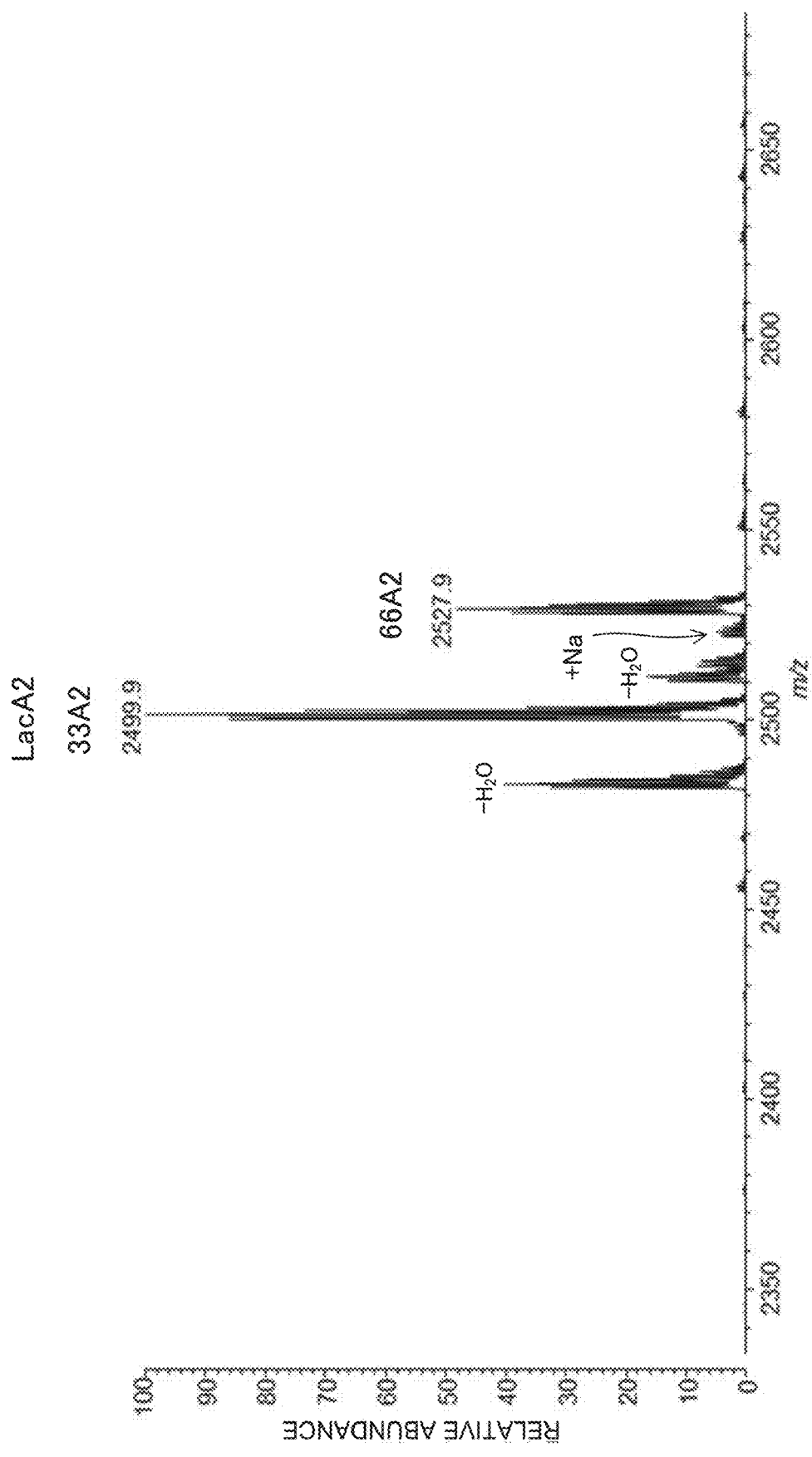
FIG. 4 shows a mass spectrum acquired in mass spectrometry in the negative ion mode for reaction products obtained through linkage-specific modification of sialic acids for glycans contained in a sample.

FIG. 4 shows the acquired mass spectrum. The peak at m/z 2527.9 corresponds to a product with isopropylamidated sialic acid, and is a peak corresponding to 66A2. The peak at m/z 2499.9 corresponds to products with ethylamidated sialic acids, and it can be interpreted that LacA2 and 33A2 were both ethylamidated and detected as substances with equal values of m/z. Therefore, the method of Comparative Example failed to distinguish between a glycan including a lactone structure originally contained in the sample and a glycan including no lactone structure originally contained in the sample.

Example 1-1

Modification of Sialic Acids

In Example 1-1, the sample was subjected to the first amidation reaction, and the linkage-specific amidation (lactonization reaction and second amidation reaction) was then performed. To the glycan sample for evaluation containing LacA2, 33A2, and 66A2 in equal moles, 20 μL of a 10% methylamine aqueous solution as the first amidation reaction solution was added, and the resultant was thoroughly stirred for redissolving. The solution obtained through the redissolving was subjected to evaporation to dryness with a SpeedVac to remove the solvent. To the sample subjected to evaporation to dryness, 20 μL of the above lactonization reaction solution was added, and the reaction was performed with stirring at 2000 rpm at room temperature for 1 hour. To the resulting reaction solution, 20 μL of a 35% ethylamine aqueous solution as the second amidation reaction solution was added, and the resultant was stirred with a vortex mixer. To the reaction solution, 160 μL of an ACN solution containing TFA was added to reach a total of 200 μL, which was then subjected to amide purification, carbon purification, and mass spectrometry. Amide purification, carbon purification, and mass spectrometry were performed in the same manner as in Comparative Example 1.

Figure 5:
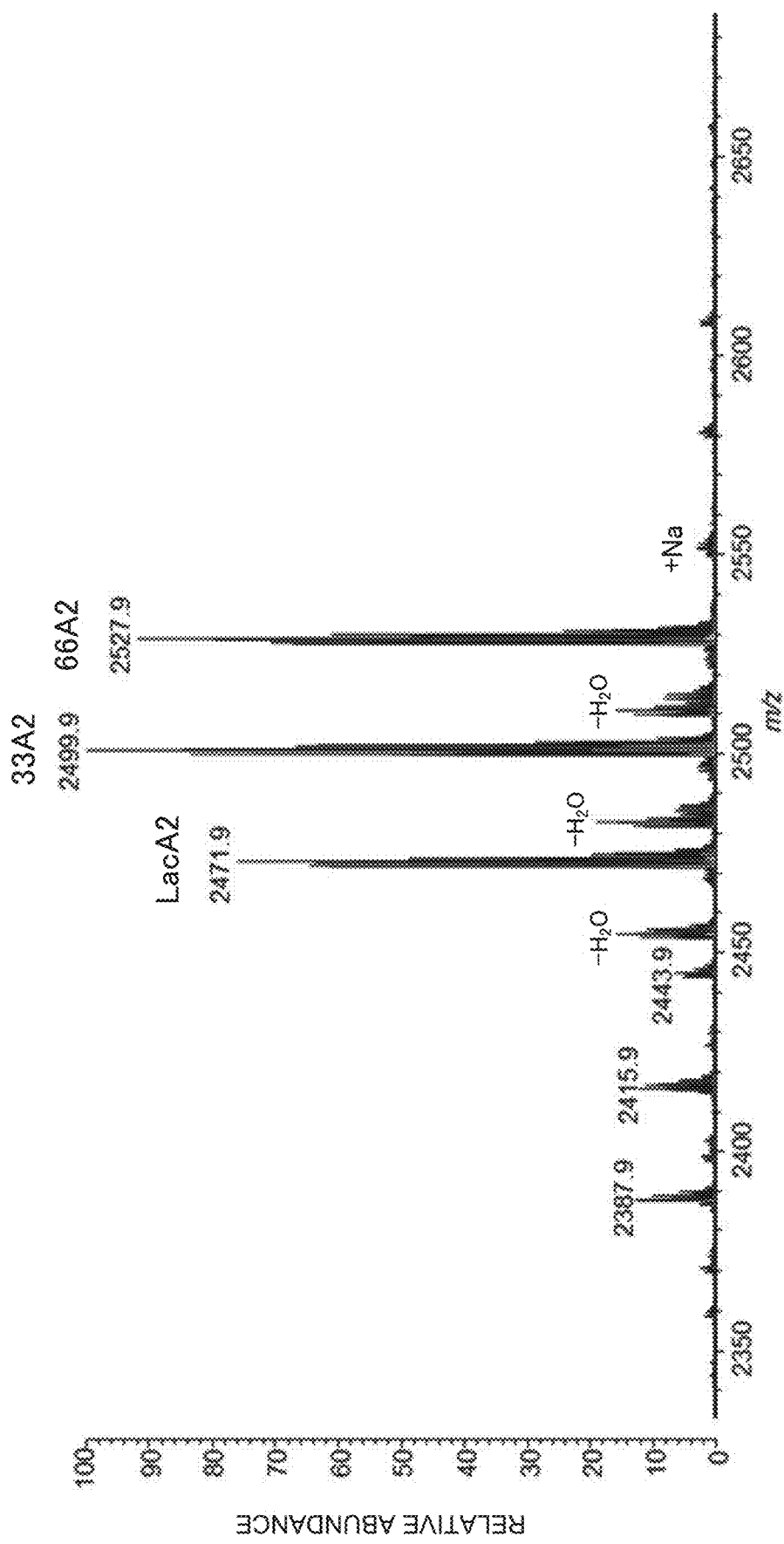
FIG. 5 shows a mass spectrum acquired in mass spectrometry in the negative ion mode for reaction products obtained through amidation of lactones and linkage-specific modification of sialic acids for glycans contained in a sample.

FIG. 5 shows the acquired mass spectrum. The peak at m/z 2527.9 corresponds to a product with isopropylamidated sialic acid, and is a peak corresponding to 66A2. The peak at m/z 2499.9 corresponds to a product with ethylamidated sialic acid, and is a peak corresponding to 33A2. The peak at m/z 2471.9 corresponds to a product with methylamidated sialic acid, and is a peak corresponding to LacA2. Thus, amidation of lactones in advance followed by linkage-specific modification of sialic acids can form modified products different in mass between a glycan with α2,3-sialic acid originally lactonized in the sample, a glycan with α2,3-sialic acid originally non-lactonized in the sample, and a glycan with α2,6-sialic acid, and the peaks for them can be identified from each other through mass spectrometry.

Example 1-2

Modification of Sialic Acids

In Example 1-2, the sample was subjected to the first amidation reaction, and then bonded to a solid phase carrier and the linkage-specific amidation (lactonization reaction and second amidation reaction) was then performed on the solid phase carrier. To the glycan sample for evaluation containing LacA2, 33A2, and 66A2 in equal moles, 20 μL of a 10% methylamine aqueous solution as the first amidation reaction solution was added, and the resultant was thoroughly stirred for redissolving. The solution obtained through the redissolving was subjected to evaporation to dryness with a SpeedVac to remove the solvent. The resulting sample was redissolved in 20 μL of $H_2O$, and bonded to a solid phase carrier including a hydrazide group as a ligand (a solid phase carrier included in the glycan purification kit BlotGlyco (Sumitomo Bakelite Co., Ltd.), the same applies hereinafter). Bonding of glycans was performed in accordance with a standard protocol for the BlotGlyco. The carrier to which glycans had been bonded was washed with 200 μL of DMSO three times. Thereafter, 100 μL of the above lactonization reaction solution was added to the carrier, and the reaction was performed with stirring at 700 rpm for 1 hour. After the liquid was removed through centrifugation, washing with 200 μL of methanol was performed three times. To the washed carrier, 100 μL of an 18% ethylamine aqueous solution as the second amidation reaction solution was added, and the resultant was lightly stirred and the solvent was then removed through centrifugation, and washing with 200 μL of $H_2O$ was performed three times. The glycan sample was released from the carrier in accordance with the standard protocol for the BlotGlyco, and subjected to evaporation to dryness with a SpeedVac. The sample subjected to evaporation to dryness was subjected to carbon purification and mass spectrometry. Carbon purification and mass spectrometry were performed in the same manner as in Comparative Example 1.

Figure 6:
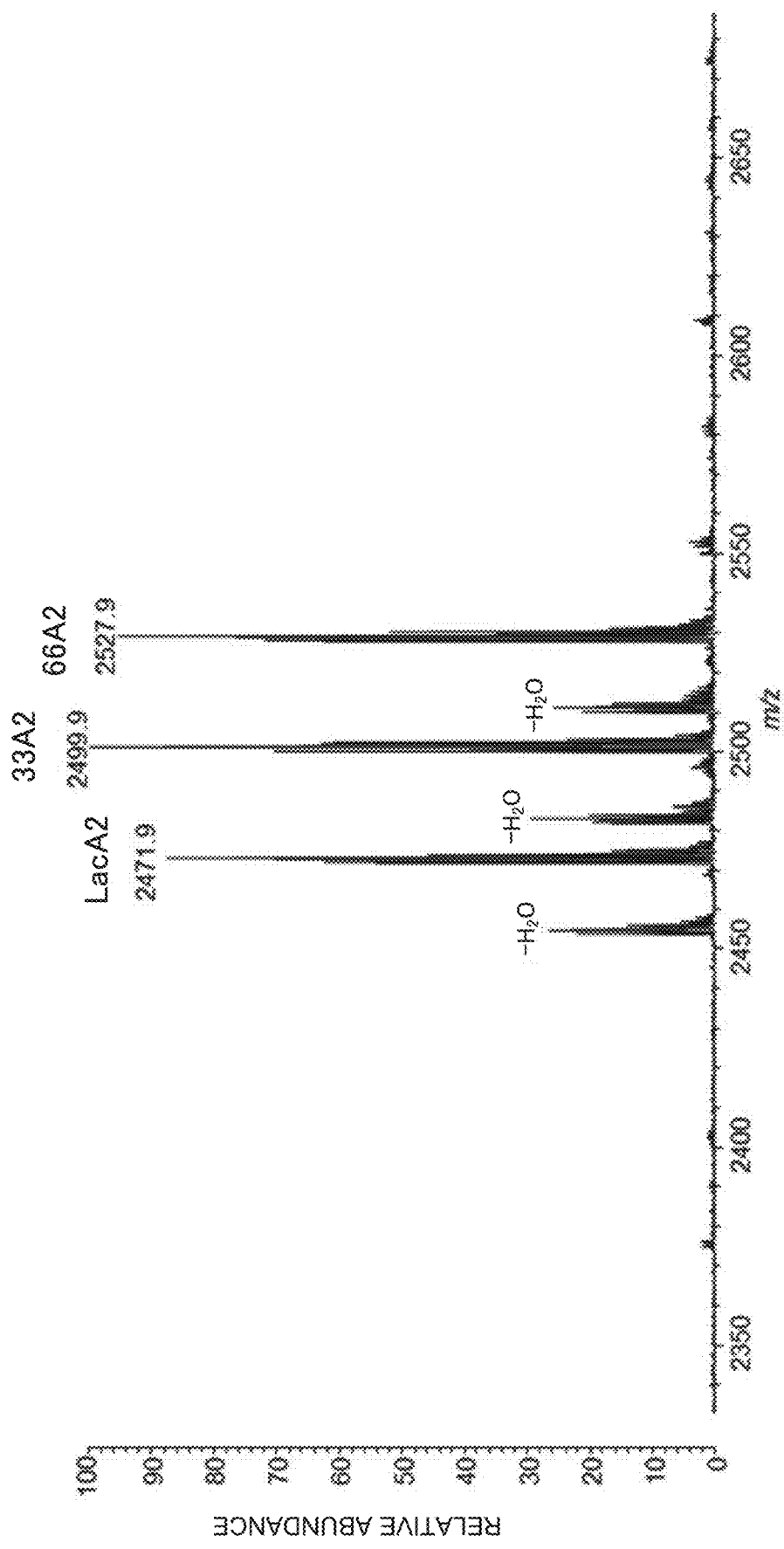
FIG. 6 shows a mass spectrum acquired in mass spectrometry in the negative ion mode for reaction products obtained through amidation of lactones, binding to hydrazide beads, and linkage-specific modification of sialic acids for glycans contained in a sample.

FIG. 6 shows the acquired mass spectrum. As with the case of Example 1-1, it is understood that LacA2, 33A2, and 66A2 were all observed as peaks at different values of m/z, and successfully distinguished from each other. Thus, a good result was obtained even when some of the reactions in the above-described first embodiment were performed with bonding to a solid phase carrier.

Comparative Example 2

Modification of Sialic Acids

In Comparative Example 2, the linkage-nonspecific amidation (nonspecific modification reaction) of sialic acids was performed without performing the first amidation. To the glycan sample for evaluation containing LacA2, 33A2, and 66A2 in equal moles, 20 μL of the nonspecific modification reaction solution (500 mM ethylamine hydrochloride, 50 mM PyAOP, 3% N-methylmorpholine, solvent: DMSO) was added, and the reaction was performed with stirring at 2000 rpm at room temperature for 1 hour. ACN and TFA were added to the reaction solution to reach a total of 200 μL, which was subjected to amide purification, carbon purification, and mass spectrometry. Amide purification, carbon purification, and mass spectrometry were performed in the same manner as in Comparative Example 1.

Figure 7:
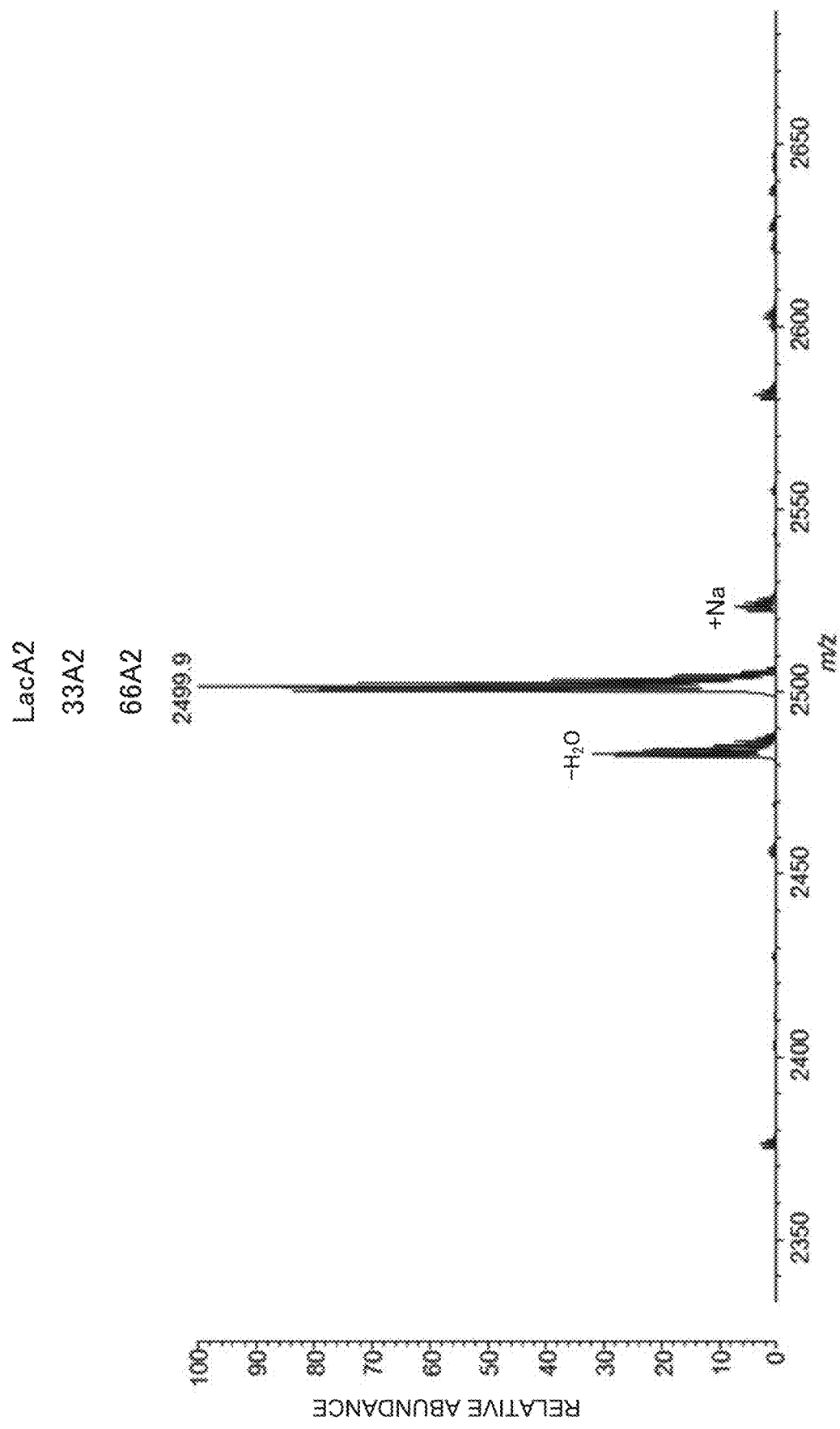
FIG. 7 shows a mass spectrum acquired in mass spectrometry in the negative ion mode for reaction products obtained through linkage-nonspecific modification of sialic acids for glycans contained in a sample.

FIG. 7 shows the acquired mass spectrum. The peak at m/z 2499.9 corresponds to products of ethylamidated sialic acids. LacA2, 33A2, and 66A2 are all ethylamidated and observed at the peak in an overlapping manner. Since linkage-nonspecific modification of sialic acids was employed in this case, α2,3-sialic acid and α2,6-sialic acid are not identifiable from each other, and the same modification is applied to lactones originally contained in the sample. Therefore, LacA2, 33A2, and 66A2 are all converted to substances with identical values of m/z, which are not identifiable from each other.

Example 2-1

Modification of Sialic Acids

In Example 2-1, the sample was subjected to the first amidation reaction, and the linkage-nonspecific amidation (nonspecific modification reaction) was then performed. To the glycan sample for evaluation containing LacA2, 33A2, and 66A2 in equal moles, 20 μL of a 10% methylamine aqueous solution as the first amidation reaction solution was added, and the resultant was thoroughly stirred for redissolving. The solution obtained through the redissolving was subjected to evaporation to dryness with a SpeedVac to remove the solvent. To the sample subjected to evaporation to dryness, 20 μL of the above nonspecific modification reaction solution described above was added, and the reaction was performed with stirring at 2000 rpm at room temperature for 1 hour. ACN and TFA were added to the reaction solution to reach a total of 200 μL, which was subjected to amide purification, carbon purification, and mass spectrometry.

Figure 8:
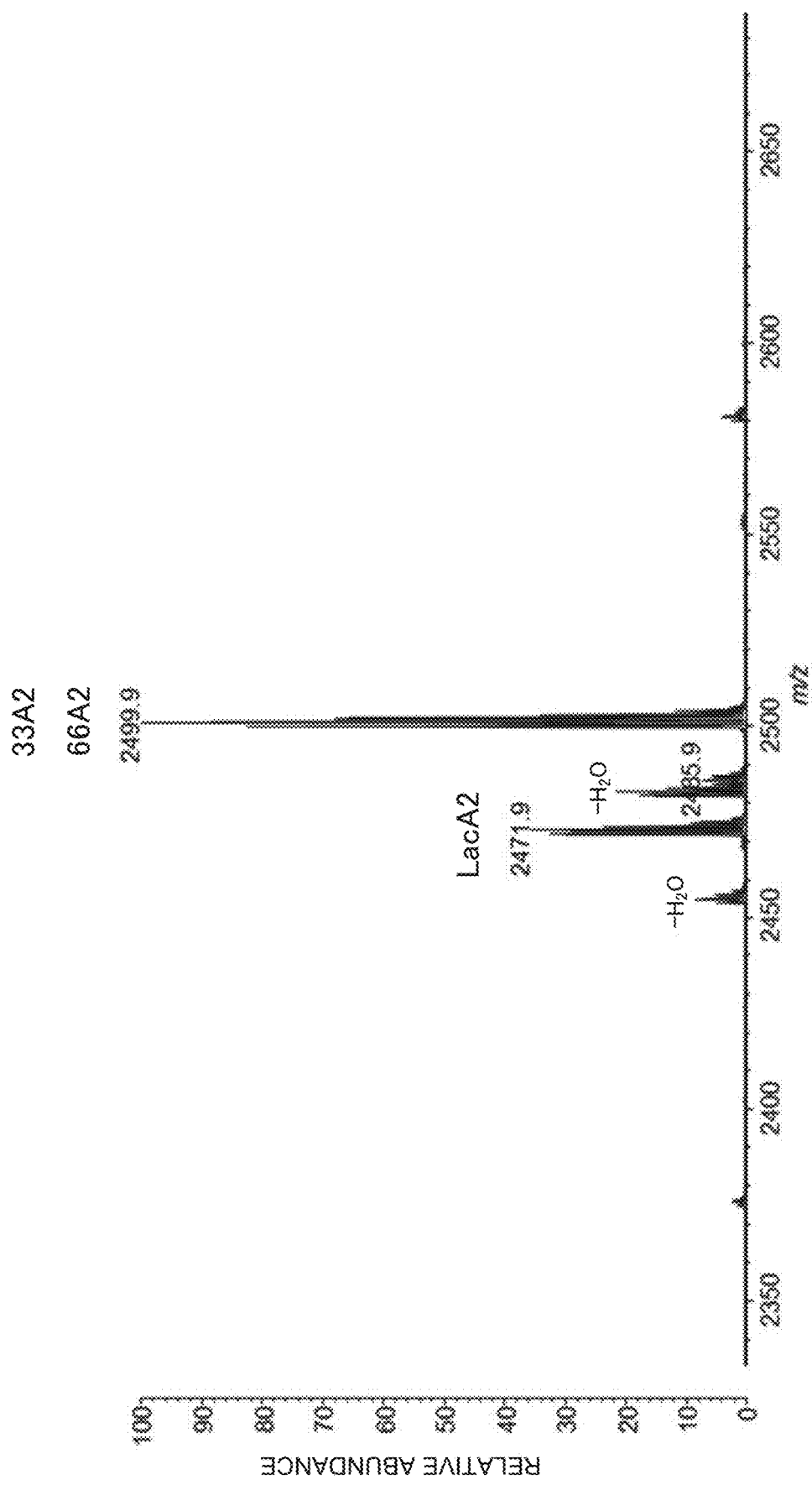
FIG. 8 shows a mass spectrum acquired in mass spectrometry in the negative ion mode for reaction products obtained through amidation of lactones and linkage-nonspecific modification of sialic acids for glycans contained in a sample.

FIG. 8 shows the acquired mass spectrum. The peak at m/z 2499.9 corresponds to products of ethylamidated sialic acids, and is a peak corresponding to 33A2 and 66A2. The peak at m/z 2471.9 corresponds to a product of methylamidated sialic acid, and is a peak corresponding to LacA2. Thus, amidation of lactones in advance followed by linkage-nonspecific modification of sialic acids can form modified products different in mass between a glycan with sialic acid originally lactonized in the sample and a glycan with sialic acid originally not lactonized in the sample, and the peaks for them can be identified from each other through mass spectrometry.

Example 2-2

Modification of Sialic Acids

In Example 2-2, the sample was subjected to the first amidation reaction, and then bonded to a solid phase carrier and the linkage-nonspecific amidation (nonspecific modification reaction) was then performed on the solid phase carrier. To the glycan sample for evaluation containing LacA2, 33A2, and 66A2 in equal moles, 20 μL of a 10% methylamine aqueous solution as the first amidation reaction solution was added, and the resultant was thoroughly stirred for redissolving. The solution obtained through the redissolving was subjected to evaporation to dryness with a SpeedVac to remove the solvent. The sample was redissolved in 20 μL of $H_2O$, and bonded to the above-mentioned solid phase carrier including a hydrazide group as a ligand (BlotGlyco). Bonding of glycans was performed in accordance with the standard protocol for the BlotGlyco. The carrier to which glycans had been bonded was washed with 200 μL of DMSO three times, and thereafter 100 μL of the above-described nonspecific modification reaction solution was added to the washed carrier, and the reaction was performed with stirring at 700 rpm for 1 hour. After the liquid was removed through centrifugation, the carrier was washed with 200 μL of methanol three times, and further washed with 200 μL of H₂O three times. Thereafter, the glycan sample after the reaction was released from the carrier in accordance with the standard protocol for the BlotGlyco, and subjected to evaporation to dryness with a SpeedVac. The sample subjected to evaporation to dryness was subjected to carbon purification and mass spectrometry. Carbon purification and mass spectrometry were performed in the same manner as in Comparative Example 1.

Figure 9:
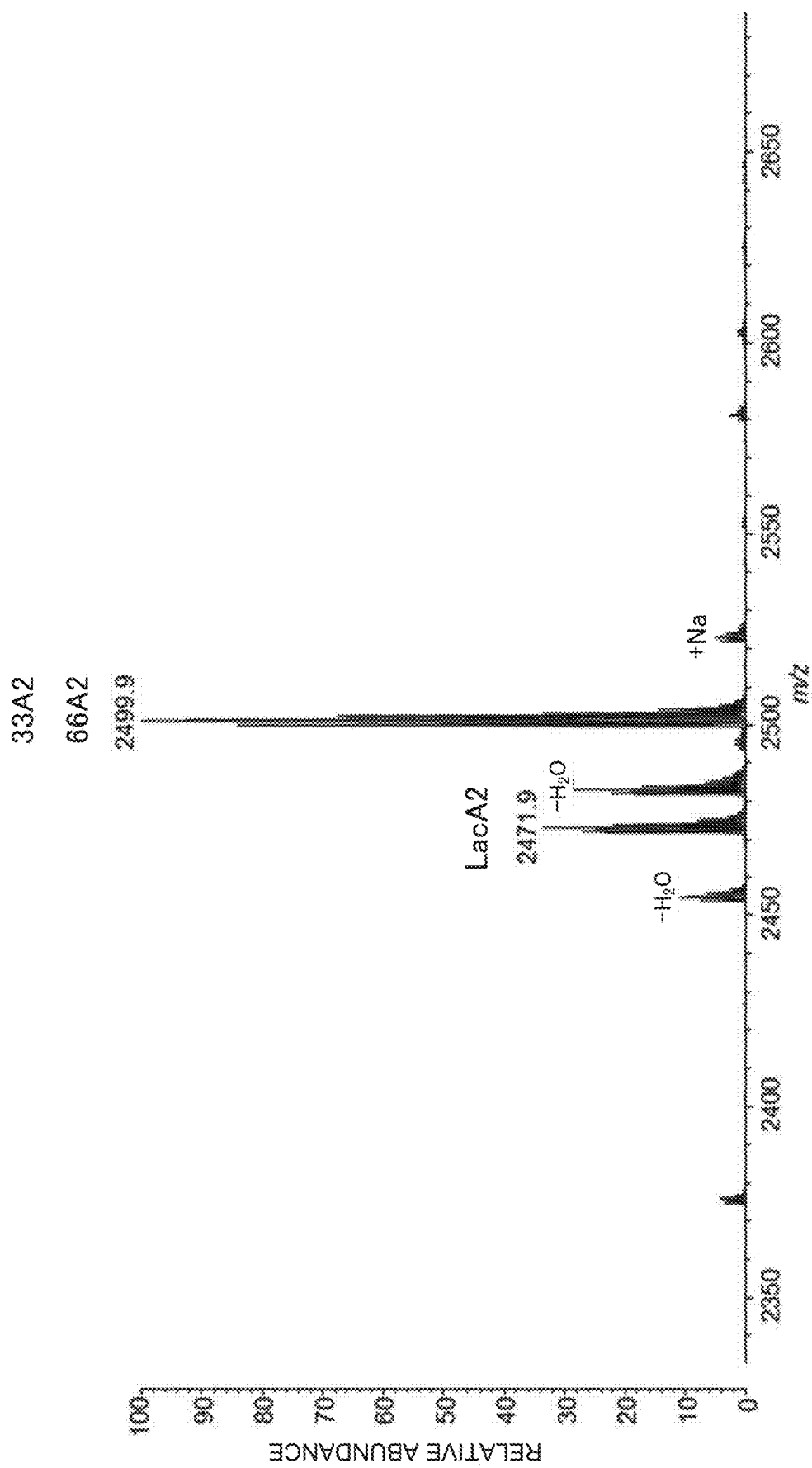
FIG. 9 shows a mass spectrum acquired in mass spectrometry in the negative ion mode for reaction products obtained through amidation of lactones, binding to hydrazide beads, and linkage-nonspecific modification of sialic acids for glycans contained in a sample.

FIG. 9 shows the acquired mass spectrum. As with the case of Example 2-1, it is understood that the peak corresponding to LacA2 and the peak corresponding to 33A2 and 66A2 were observed as peaks at different values of m/z, and successfully distinguished from each other. Thus, a good result was obtained even when some of the reactions in the above-described second embodiment were performed with bonding to a solid phase carrier.

Examination on Aminolysis

Examples below, which do not involve modification of lactones originally contained in a sample in contrast to the methods for preparing an analytical sample in the above-described embodiments, demonstrate that a solution containing amine causes aminolysis of a lactone formed in a sialic acid in a glycan. In the following description, "lactonization reaction" and "amidation reaction" respectively correspond to "lactonization reaction" and "second amidation reaction" in the above-described embodiments. "Amidation reaction solution" is one selected under the same conditions as for the first amidation reaction solution or the second amidation reaction solution in the above-described embodiments.

Examination on Amine Concentration in Amidation Reaction

A glycan was cleaved and released with PNGaseF from α2,3-SGP including α2,3-linked sialic acid, and used as a sample. The sialylglycopeptide was one in which a glycan was linked to a peptide of several residues. The sample was bonded to a solid phase carrier (BlotGlyco; Sumitomo Bakelite Co., Ltd.) consisting of beads having a hydrazide group as a ligand. The bonding of the glycan to the solid phase carrier was performed according to a standard protocol of the glycan purification kit BlotGlyco.

The carrier to which the glycan had been bonded was washed three times with 200 μL of DMSO. Thereafter, 100 μL of a lactonization reaction solution containing isopropylamine (2 M isopropylamine hydrochloride, 500 mM EDC-HCl, 500 mM HOBt) was added thereto, and the reaction was performed with mild stirring at 800 rpm for 1 hour. Through this operation, α2,6-sialic acid and α2,3-sialic acid were converted into isopropylamide and the lactone form, respectively. The reaction solution was removed through centrifugation, and washing was then performed once with 200 μL of methanol. Thereafter, the lactone was subjected to an amidation reaction through three times of washing with 200 μL of methylamine aqueous solution (concentration: 0.1% to 10%). Subsequently, washing was performed twice with 200 μL of methanol and three times with 200 μL of water. Thereafter, the reacted glycan sample was released from the carrier by using a method according to the standard protocol, and subjected to desalting and purification by using a Stage Tip Carbon followed by evaporation to dryness through centrifugal concentration (SpeedVac). The sample subjected to evaporation to dryness was redissolved in 10 μL of water, and 1 μL was taken therefrom and dropped on a focus plate, and 0.5 μL of 100 mM 3AQ/CA and 2 mM ammonium sulfate dissolved in 50% acetonitrile (ACN), in which 3AQ/CA was used as a matrix, was added thereto, and the resultant was then reacted on a heat block at 75° C. for 1.5 hours for labeling of reducing ends of the glycan with 3AQ. After the completion of the reaction, the plate was cooled to room temperature, and time-of-flight mass spectrometry was performed through MALDI-QIT-TOF-MS (AXIMA-Resonance, Shimadzu/Kratos) in the negative ion mode.

FIG. 10 shows mass spectra when aminolysis was caused by using (a) 1% or (b) 10% methylamine aqueous solution as the amidation reaction solution. 33A2 (corresponding to FIG. 3B) released from α2,3-SGP as the sample had been subjected to intramolecular dehydration condensation with the above lactonization reaction solution for conversion into the lactone form (corresponding to FIG. 3A). In this case, the hydrazide beads were then washed only with the methylamine solution without using any dehydration condensation agent. Nevertheless, it can be seen that the original lactone structure was methylamidated (corresponding to the peak at m/z 2471.9). The peak observed at m/z 2360.9 indicates one carboxy group left without being bonded to methylamine. This peak is inferred to correspond to a glycan which underwent not aminolysis but hydrolysis of lactone. For the amidation reaction with 10% methylamine aqueous solution, this peak derived from hydrolysis was further weaker, indicating that aminolysis occurred in an almost exclusive manner.

Figure 11:
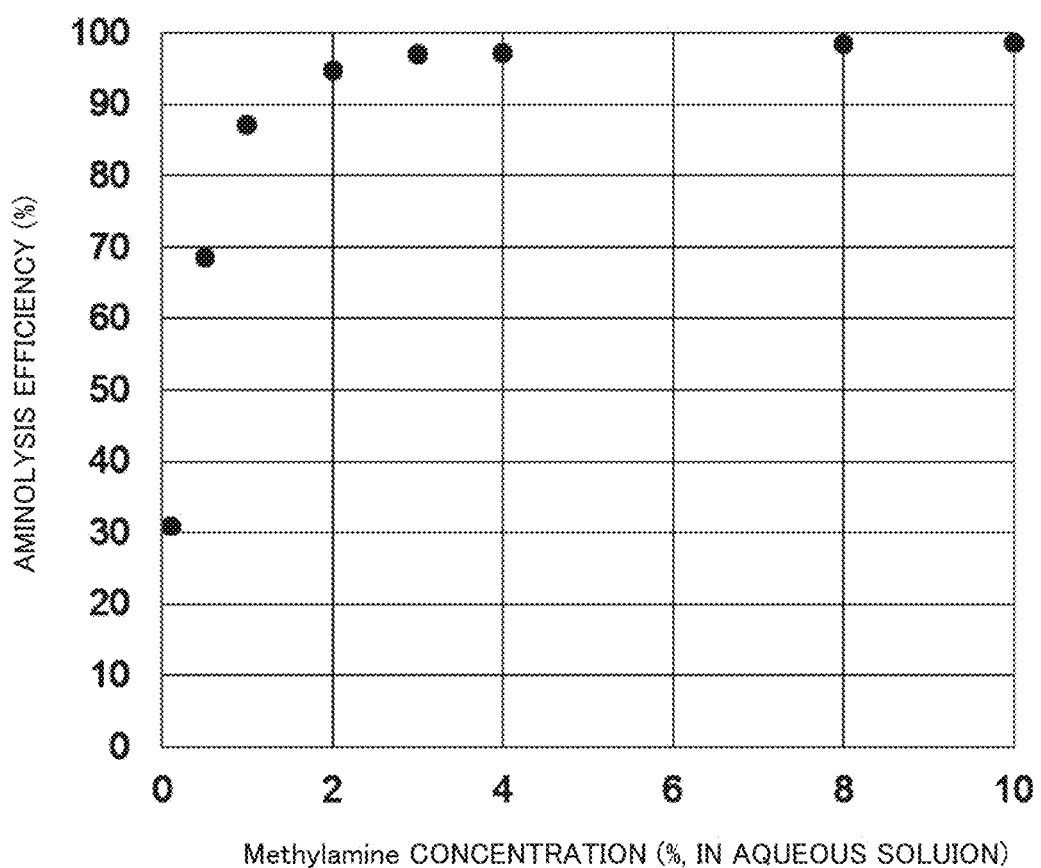
FIG. 11 shows a graph representing the relation between the concentration of methylamine aqueous solution and the efficiency of amidation in the aminolysis.

FIG. 11 shows a graph representing ratios of sialic acids which underwent aminolysis in contrast to those which underwent hydrolysis (aminolysis efficiency) calculated from the peak signal intensities in the mass spectra against methylamine concentrations of the amidation reaction solution. Although aminolysis sufficiently occurred even when the concentration of methylamine solution was 1%, it can be seen that aminolysis was successfully caused in a more efficient manner with use of an amidation reaction solution containing a higher concentration of methylamine.

Examination on Type of Amine in Amidation Reaction

Figure 12:
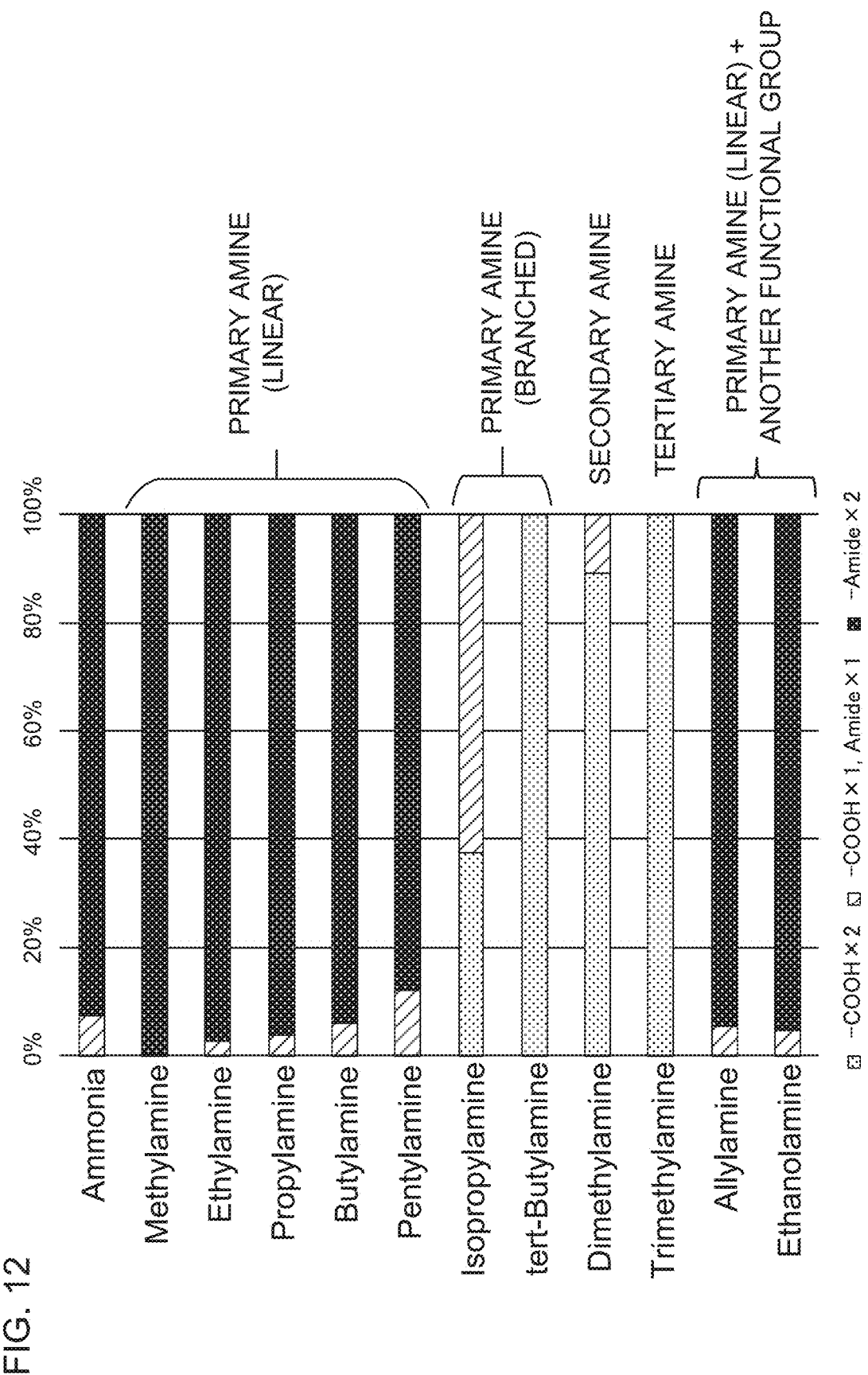
FIG. 12 shows graphs representing the types of amine in the aminolysis and respective production ratios of reaction products.

FIG. 12 shows graphs representing a production ratio in each amidation reaction with 3 M aqueous ammonia or alkylamine aqueous solution (in a concentration corresponding to 10% for methylamine) as the amidation reaction solution under a condition generally identical to those in the above examination on the amine concentration.

The results in FIG. 12 show that while aminolysis was successfully caused in an efficient manner for ammonia and unbranched primary alkylamines, the aminolysis efficiency was low and hydrolysis (production of —COOH) was dominant for branched alkylamines including isopropylamine and tert-butylamine. When a tertiary amine was used for the amidation reaction solution, only hydrolysis occurred because the tertiary amine does not inherently react even in the presence of a dehydration condensation agent. Even when a secondary amine was used, the secondary amine did not react well, and hydrolysis dominantly occurred. For allylamine and ethanolamine, aminolysis dominantly occurred. These results revealed that any primary amine at least having no branch in the hydrocarbon chain is acceptable even if the primary amine includes another functional group, and a double bond or a hydroxy group may be included in the primary amine. Thus, it is understood that primary amines having no branch in the carbon chain are particularly suitable for the occurrence of aminolysis.

Examination on Solvent in Amidation Reaction

Figure 13:
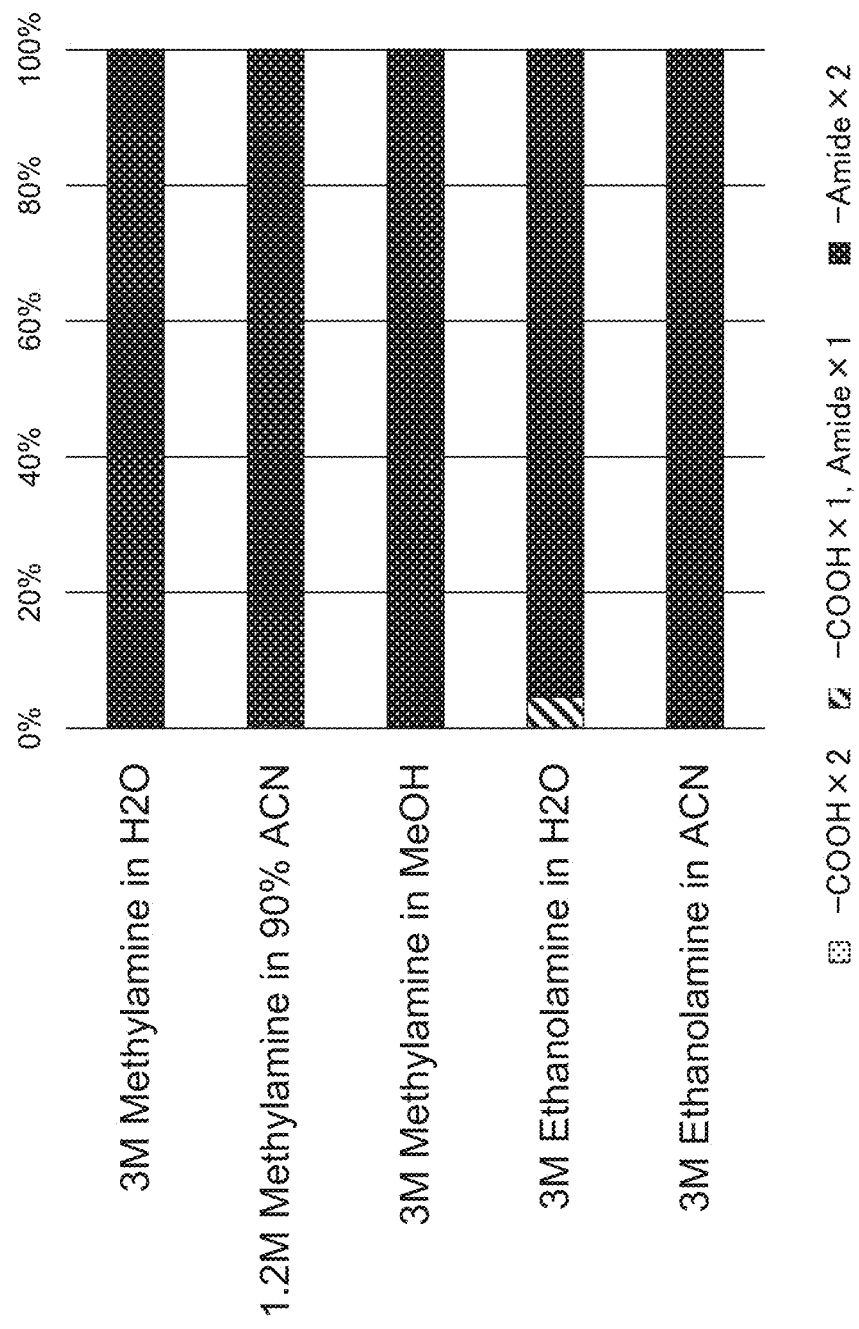
FIG. 13 shows graphs representing the types of amine and solvent in the aminolysis and respective production ratios of reaction products.

FIG. 13 shows graphs representing production ratios with 1.2 M methylamine dissolved in 90% ACN, 3 M methylamine dissolved in methanol, or 3 M ethanolamine dissolved in ACN, etc., as the amidation reaction solution, under conditions generally identical to those in the above examination.

The results in FIG. 13 show that aminolysis occurred with a high fraction for each case, and the peak corresponding to an amidated glycan was dominantly observed. Amidation occurred without any problem even when an amine dissolved in methanol or ACN substantially free of water was used, which strongly suggests that there occurred not amidation following temporary hydrolysis of a lactone but aminolysis to amidate by the direct action of amine on a lactone. Hydrolysis was more suppressed under conditions substantially free of water, and amidation occurred in an almost exclusive manner even when ethanolamine, which caused hydrolysis to around 5% of sialic acids in water solvent, was used for the amidation reaction solution.

Examination on pH in Amidation Reaction

Figure 14:
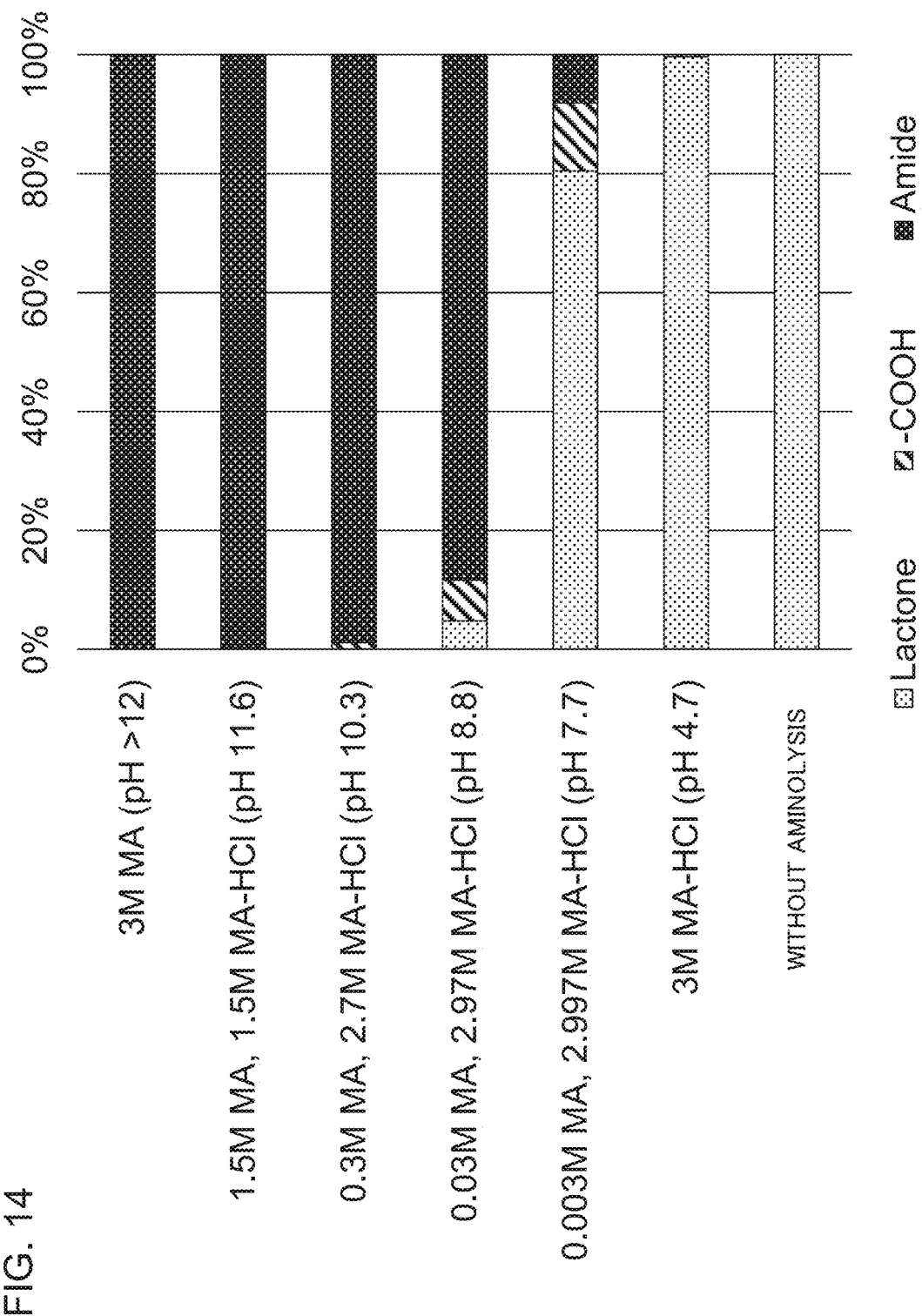
FIG. 14 shows graphs representing pH in the aminolysis and respective production ratios of reaction products.

FIG. 14 shows graphs representing production ratios with amidation reaction solutions prepared by mixing 3 M methylamine aqueous solution and 3 M methylamine hydrochloride aqueous solution at arbitrary ratios under conditions generally identical to those in the above examination. "MA" and "MA-HCl" in FIG. 14 represent methylamine aqueous solution and methylamine hydrochloride aqueous solution, respectively.

In the present examination, it was expected that α2,3-sialic acid would remain as a lactone even after addition of the amidation reaction solution to the sample under some conditions. Accordingly, to more quantitatively evaluate an unstable lactone, the amidation reaction solution was added to the sample for an amidation reaction, washing was then performed twice with 200 µL of H$_2$O and twice with 200 µL of ACN, and another amidation reaction was subsequently performed with an amidation reaction solution containing 3 M ethanolamine dissolved in ACN. Under conditions for this two-step amidation reaction, amidated products of the first-step amidation reaction (detected as a methylamidated form), hydrolyzed products (detected as —COOH), and products remaining as lactones (detected as an amidated form with ethanolamine) can be clearly discriminated. The amidation reaction in the present examination was performed not through three times of washing performed in the above with 200 µL of the amidation reaction solution, but through adding 100 µL of the amidation reaction solution followed by stirring at 700 rpm for 2 minutes.

The results in FIG. 14 show that aminolysis hardly occurred when the amidation reaction solution was not added ("without aminolysis") or when 3 M methylamine hydrochloride solution (pH 4.7) was used as the amidation reaction solution, and substantially all the sialic acids were remaining as lactones. When the ratio of methylamine solution in preparing the amidation reaction solution was raised to increase pH, the sialic acids gradually underwent hydrolysis and aminolysis, and around 90% of the sialic acids were amidated at pH 8.8, and substantially all the sialic acids were amidated with an amidation reaction solution at pH 10.3 or higher.

Examination on Amidation Reaction Using Sample of Glycan Released from Fetuin

The glycoprotein fetuin was dissolved in 20 mM ammonium bicarbonate, 10 mM DTT, and 0.02% SDS, and treated at 100° C. for 3 minutes for denaturation and reduction. Thereafter, the resultant was cooled to room temperature, and PNGase F was added thereto, and the resultant was incubated at 37° C. overnight to release the glycan. The next day, the PNGase F was deactivated by heating at 100° C. for 3 minutes to terminate the enzyme reaction.

The released glycan was bonded to hydrazide beads and subjected to linkage-specific modification with a lactonization reaction solution containing isopropylamine as in the above examination, and then subjected to an amidation reaction with 10% methylamine aqueous solution. Elution from the beads and detection by using mass spectrometry were performed as in the above examination.

Figure 15:
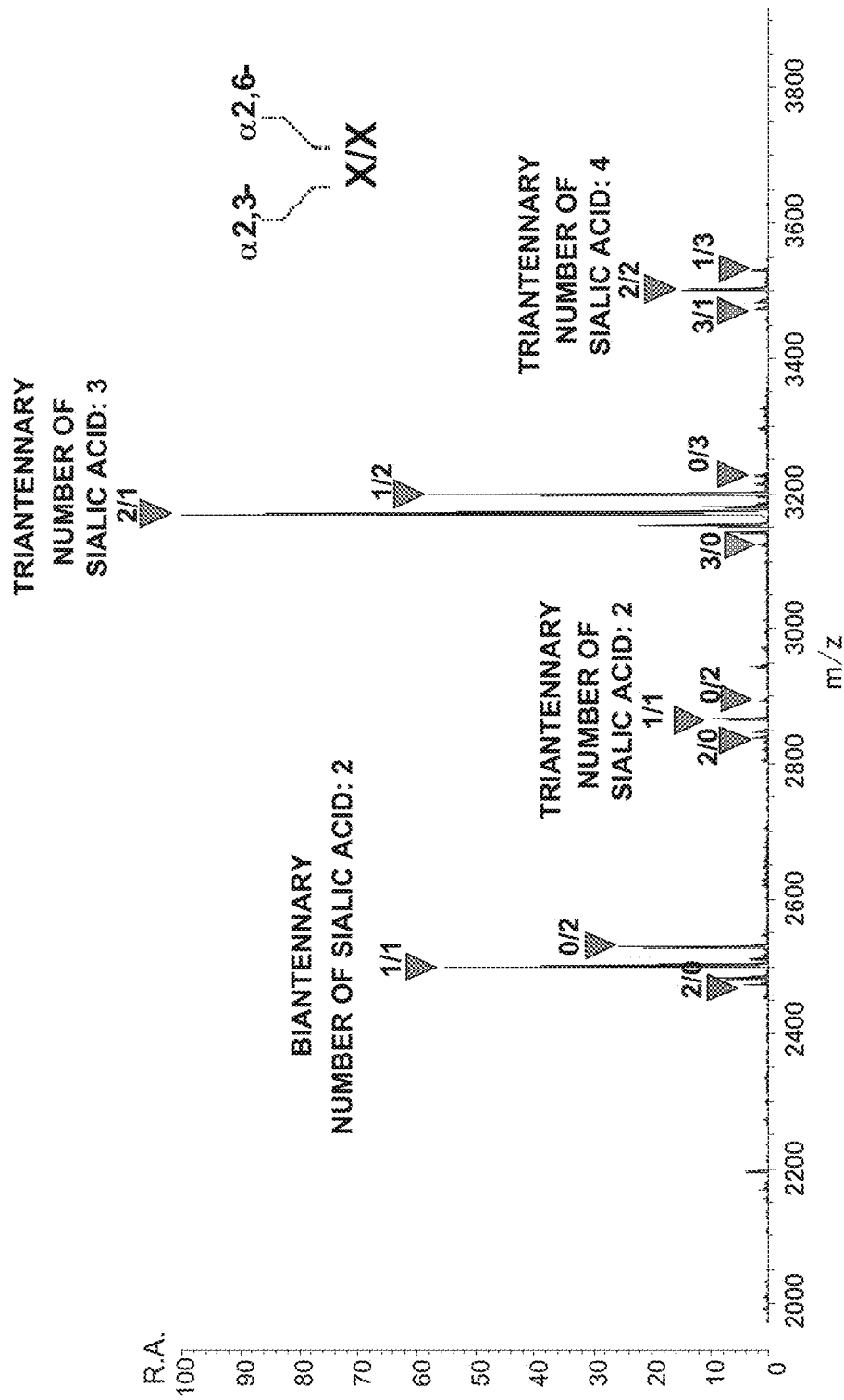
FIG. 15 shows a mass spectrum acquired in mass spectrometry for reaction products obtained through a lactonization reaction and aminolysis of a glycan released from the glycoprotein fetuin.

FIG. 15 shows a mass spectrum for the glycan released from fetuin. Among numerals at each peak, the left numeral denotes the number of α2,3-sialic acids included in the molecule corresponding to the peak, and the right numeral denotes the number of α2,6-sialic acids included in the same molecule. Neither a product of hydrolysis nor an unreacted form was detected, which indicates that lactonized sialic acids were efficiently methylamidated. Comparison between this mass spectrum and mass spectra reported in PTL 1 and NPTL3 teaches that the lactone was directly methylamidated through aminolysis in an efficient manner even without undergoing an amidation reaction with a dehydration condensation agent.

Examination on Amidation Reaction on HILIC Carrier

α2,3-SGP was dissolved in 20 mM ammonium bicarbonate, and PNGase F was added thereto, and the resultant was incubated at 37° C. overnight to release the glycan. The next day, the PNGase F was deactivated by heating at 100° C. for 3 minutes to terminate the enzyme reaction. Thereafter, the resultant was desalted with a Stage Tip Carbon, and subjected to evaporation to dryness in an Eppendorf tube by using a SpeedVac.

Thereafter, 20 µL of a lactonization reaction solution containing isopropylamine (2 M isopropylamine hydrochloride, 500 mM EDC-HCl, 500 mM HOBt) was added thereto, and the reaction was performed with stirring at 2000 rpm for 1 hour. Subsequently, the resultant was diluted with 120 µL of ACN, which was added to an Amide Tip (GL Science Inc.) and passed therethrough by centrifugation at 4000×g to allow the glycan to be adsorbed on a carrier including an amide group for HILIC. Then, 20 to 200 µL of 90% ACN/4% methylamine solution as the amidation reaction solution was passed therethrough for an amidation reaction. Further, 100 µL of 90% ACN/0.1% TFA was passed twice therethrough for washing, and finally 20 µL of H$_2$O was passed twice therethrough for elution of the glycan, and the elute was subjected to evaporation to dryness by using a SpeedVac. Thereafter, the resultant was further desalted with a Stage Tip Carbon, and subjected to on-target 3AQ, as in the above examination, followed by mass spectrometry.

Figure 16:
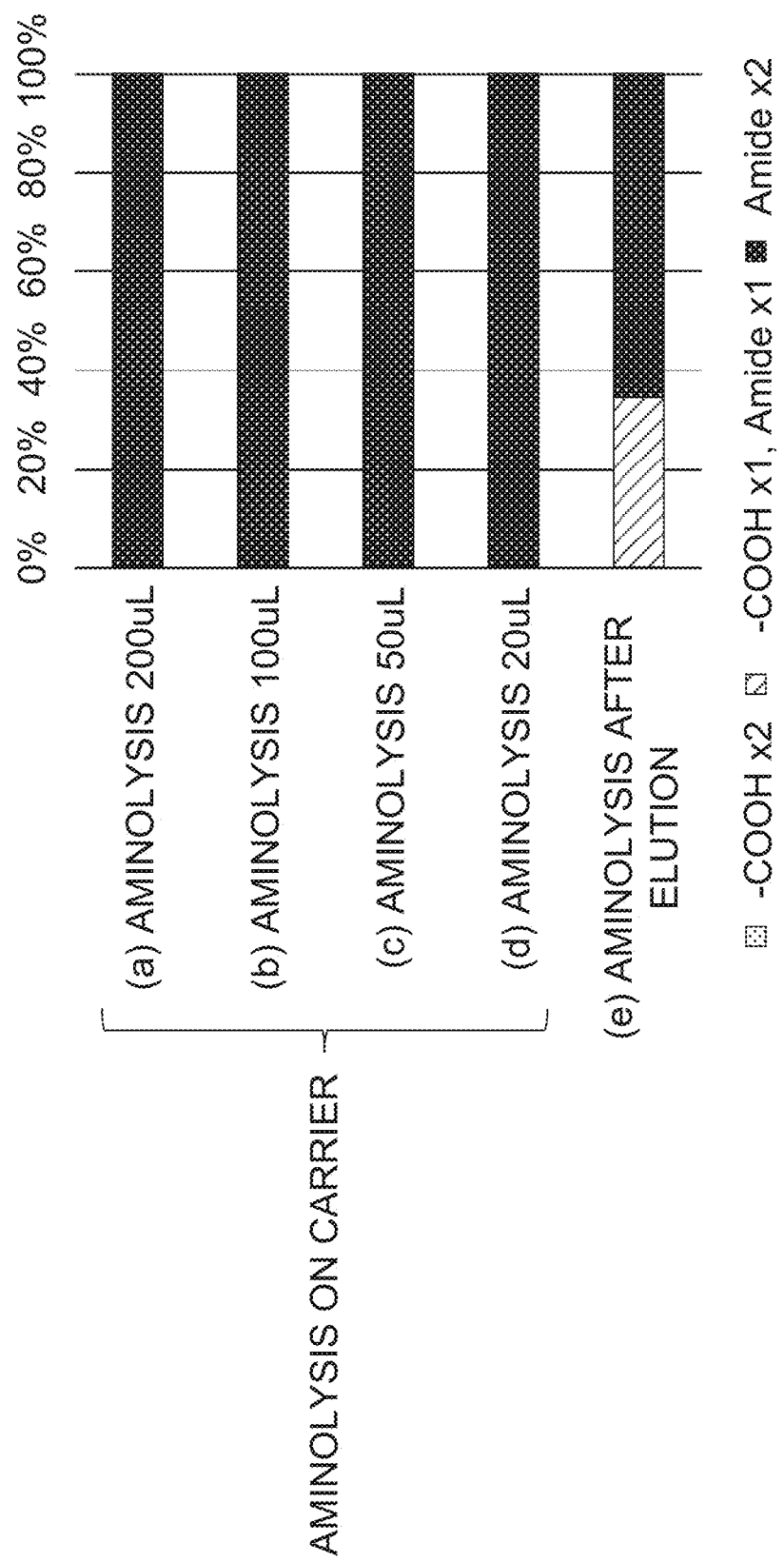
FIG. 16 shows graphs representing respective production ratios of reaction products obtained when a glycan released from α2,3-sialylglycopeptide was subjected to a lactonization reaction and then bonded to an HILIC carrier and the resultant was subjected to aminolysis before or after elution.

In FIG. 16, (a) to (d) show graphs representing the respective amounts of the amidation reaction solution and production ratios. It was found that aminolysis proceeded in an almost exclusive manner for all of (a) to (d). When the amount of the amidation reaction solution was as small as 20 µL, the time of contact between the carrier and the amidation reaction solution was expected to be several tens of seconds at most, suggesting that the reaction of aminolysis very quickly occurred.

Examination on Amidation Reaction After Purification with HILIC

By using the operation as in the above examination, a glycan was cleaved and released from α2,3-SGP, and a lactonization reaction solution containing isopropylamine was added to the glycan for reaction, and ACN was added thereto for dilution, and the glycan was allowed to be adsorbed on an HILIC carrier. Thereafter, 100 µL of 90% ACN/0.1% TFA solution was passed twice therethrough for washing, and finally 20 μL of H$_2$O was passed twice therethrough for elution of the glycan. Thereto, 6.7 μL of 40% methylamine aqueous solution was added to form an amidation reaction solution containing methylamine with a final concentration of 10%, and the resultant was lightly stirred and then left to stand at room temperature for 2 minutes for an amidation reaction. Thereafter, the solvent was removed by using a SpeedVac, and the resultant was further desalted with a Stage Tip Carbon, and subjected to on-target 3AQ, as in the above examination, followed by mass spectrometry.

In FIG. 16, (e) shows the result. Although the lactones in the sample were generally methylamidated, a product of hydrolysis was also detected. The reason is, in our interpretation, that after the lactonization reaction solution containing isopropylamine was removed by the HILIC carrier, a part of the lactones underwent hydrolysis during the process of washing the carrier. Therefore, although the amidation reaction solution may be added to a sample eluted from a HILIC carrier, it is preferable to add the amidation reaction solution in a state in which a sample is adsorbed on an HILIC carrier, for the purpose of causing aminolysis for substantially all lactones to maximize the reaction efficiency.

The invention claimed is:

1. A method for preparing an analytical sample for analysis of a glycan that includes a lactone structure and is contained in a sample, the method comprising:
    performing a first amidation reaction that amidates a sialic acid including the lactone structure through addition of a first amidation reaction solution to the sample, the first amidation reaction solution containing ammonia, an amine, or a salt thereof as a first nucleophilic agent that is reacted with the sialic acid including the lactone structure; and
    performing a second reaction that modifies at least a part of sialic acids not amidated in the first amidation reaction through a method different from permethylation.

2. The method for preparing an analytical sample according to claim 1, wherein
    a time during which the sample is in contact with the first amidation reaction solution in order to perform the first amidation reaction is shorter than 30 minutes.

3. The method for preparing an analytical sample according to claim 1, wherein:
    the first amidation reaction solution does not include a dehydration condensation agent that is reacted with the sialic acid.

4. The method for preparing an analytical sample according to claim 1, wherein:
    the amine is a primary amine.

5. The method for preparing an analytical sample according to claim 1, wherein:
    the amine includes an alkyl group.

6. The method for preparing an analytical sample according to claim 5, wherein:
    the alkyl group is unbranched.

7. The method for preparing an analytical sample according to claim 1, wherein:
    pH of the first amidation reaction solution is 8.0 or higher.

8. The method for preparing an analytical sample according to claim 1, wherein
    the first amidation reaction solution contains an amine or a salt thereof, and
    a concentration of the amine or salt thereof is 0.5 M or more.

9. The method for preparing an analytical sample according to claim 1, wherein:
    the second reaction is performed in a state in which the sample is bonded to or adsorbed on a solid phase carrier.

10. The method for preparing an analytical sample according to claim 1, wherein:
    the sample subjected to the first amidation reaction is contacted with a second reaction solution in the second reaction,
    the second reaction solution contains ammonia, an amine, an alcohol, or a salt thereof as a second nucleophilic agent that is reacted with a sialic acid not amidated in the first amidation reaction,
    at least a part of sialic acids that does not include the lactone structure and is contained in the sample before the first amidation reaction is amidated or esterified through the second reaction, and
    the first nucleophilic agent and the second nucleophilic agent are different.

11. The method for preparing an analytical sample according to claim 10, wherein
    the second reaction solution contains a dehydration condensation agent.

12. The method for preparing an analytical sample according to claim 1, wherein
    the sample subjected to the first amidation reaction is contacted with a second reaction solution in the second reaction, and
    the second reaction solution contains an alkylating agent for ester synthesis.

13. The method for preparing an analytical sample according to claim 1, wherein
    at least a part of the sialic acids is modified based on a linkage type of the sialic acid in the second reaction.

14. The method for preparing an analytical sample according to claim 13, wherein
    α2,6-sialic acid and at least one of α2,3-sialic acid, α2,8-sialic acid and α2,9-sialic acid are modified into different modified products in the second reaction.

15. An analysis method comprising:
    preparing an analytical sample by using the method for preparing an analytical sample according to claim 1; and
    analyzing the prepared analytical sample.

16. The analysis method according to claim 15, wherein:
    the prepared analytical sample is analyzed through at least one of mass spectrometry and chromatography.

* * * * *